(12) United States Patent
Segale et al.

(10) Patent No.: US 11,667,957 B2
(45) Date of Patent: Jun. 6, 2023

(54) METHODS AND COMPOSITIONS FOR IDENTIFYING LIGANDS ON ARRAYS USING INDEXES AND BARCODES

(71) Applicant: Illumina, Inc., San Diego, CA (US)

(72) Inventors: Darren Segale, San Diego, CA (US); Fiona E. Black, Encinitas, CA (US); Jeffrey Dennis Brodin, San Diego, CA (US); Jeffrey Fisher, San Diego, CA (US); Lorenzo Berti, San Diego, CA (US); Siew Hong Leong, Singapore (SG)

(73) Assignee: Illumina, Inc., San Diego, CA (US)

( * ) Notice: Subject to any disclaimer, the term of this patent is extended or adjusted under 35 U.S.C. 154(b) by 530 days.

(21) Appl. No.: 16/661,885

(22) Filed: Oct. 23, 2019

(65) Prior Publication Data

US 2020/0131570 A1  Apr. 30, 2020

Related U.S. Application Data

(60) Provisional application No. 62/903,108, filed on Sep. 20, 2019, provisional application No. 62/750,370, filed on Oct. 25, 2018.

(51) Int. Cl.
*C12Q 1/6816* (2018.01)
*C12Q 1/6837* (2018.01)

(52) U.S. Cl.
CPC .................................. *C12Q 1/6816* (2013.01)

(58) Field of Classification Search
None
See application file for complete search history.

(56) References Cited

U.S. PATENT DOCUMENTS

| | | |
|---|---|---|
| 4,971,903 A | 11/1990 | Hyman |
| 5,599,675 A | 2/1997 | Brenner |
| 5,750,341 A | 5/1998 | Macevicz |
| 6,210,891 B1 | 4/2001 | Nyren |
| 6,258,568 B1 | 7/2001 | Nyren |
| 7,115,400 B1 | 10/2006 | Adessi |

(Continued)

FOREIGN PATENT DOCUMENTS

| | | |
|---|---|---|
| WO | WO 2018/064640 | 4/2018 |
| WO | WO 2018/174827 | 9/2018 |

OTHER PUBLICATIONS

Bibikova et al., Quantitative Gene Expression Profiling in Formalin-Fixed, Paraffin-Embedded Tissues Using Universal Bead Arrays, Am J Pathol 165:1799-807 (2004).
Bibikova et al., High-throughput DNA methylation profiling using universal bead arrays, Genome Res 16:383-93 (2006).
Fan et al., Highly Parallel SNP Genotyping, Cold Spring Harb Symp Quant Biol 68:69-78 (2003).
(Continued)

*Primary Examiner* — Robert T. Crow
(74) *Attorney, Agent, or Firm* — Knobbe, Martens, Olson & Bear LLP

(57) ABSTRACT

Some embodiments provided herein include methods and compositions for the detection of target ligands on an array. In some embodiments, a capture probe specifically binds to a target ligand from a sample, the location of a bead comprising the capture probe in an array is determined, and the bead is decoded to identify the capture probe and the sample. In some embodiments, a barcode is indicative of a capture probe attached to a bead; and an index is indicative of a subpopulation of beads. In some embodiments, the barcode and the index are determined by sequencing.

20 Claims, 11 Drawing Sheets

(56) References Cited

U.S. PATENT DOCUMENTS

| | | |
|---|---|---|
| 7,985,565 B2 | 7/2011 | Mayer |
| 8,053,192 B2 | 11/2011 | Bignell |
| 9,045,796 B2 | 6/2015 | Gunderson |
| 9,441,267 B2 | 9/2016 | Gunderson |
| 2003/0157504 A1* | 8/2003 | Chee .................... C12Q 1/6837 435/6.11 |
| 2005/0130173 A1 | 6/2005 | Leamon |
| 2005/0181394 A1 | 8/2005 | Steemers |
| 2006/0134633 A1 | 6/2006 | Chen |
| 2015/0337295 A1 | 11/2015 | West |
| 2017/0240963 A1 | 8/2017 | Amorese |
| 2017/0327876 A1 | 11/2017 | Khafizov |
| 2017/0349939 A1* | 12/2017 | Metzker ................ C12Q 1/686 |
| 2018/0291369 A1 | 10/2018 | Wang |

OTHER PUBLICATIONS

Fan et al., A Versatile Assay for High-Throughput Gene Expression Profiling on Universal Array Matrices, Genome Res 14:878-85 (2004).

Gunderson et al., A genome-wide scalable SNP genotyping assay using microarray technology, Nat Genet 37:549-54 (2005).

Kuhn et al., A novel, high-performance random array platform for quantitative gene expression profiling, Genome Res 14:2347-56 (2004).

Michael et al., Randomly Ordered Addressable High-Density Optical Sensor Arrays, Anal Chem 70, 1242-8 (1998).

Walt, Bead-based Fiber-Optic Arrays, Science 287, 451-2 (2000).

Yeakley et al., Profiling alternative splicing on fiber-optic arrays, Nat Biotechnol 20:353-8 (2002).

\* cited by examiner

METHODS AND COMPOSITIONS FOR IDENTIFYING LIGANDS ON ARRAYS USING INDEXES AND BARCODES

RELATED APPLICATIONS

This application claims priority to U.S. Prov. App. Ser. No. 62/903,108 filed Sep. 20, 2019 entitled "METHODS AND COMPOSITIONS FOR HIGH-THROUGHPUT GENOTYPING ON ARRAYS USING INDEXES AND BARCODES"; and to U.S. Prov. App. No. 62/750,370 filed Oct. 25, 2018 entitled "POSITIONAL IDENTIFICATION OF MICROFEATURES IN ARRAYS USING BARCODES" which are each incorporated by reference in its entirety.

FIELD OF THE INVENTION

Some embodiments provided herein include methods and compositions for the detection of target ligands on an array. In some embodiments, a capture probe specifically binds to a target ligand from a sample, the location of a bead comprising the capture probe in an array is determined, and the bead is decoded to identify the capture probe and the sample. In some embodiments, a barcode is indicative of a capture probe attached to a bead; and an index is indicative of a subpopulation of beads. In some embodiments, the barcode and the index are determined by sequencing.

BACKGROUND OF THE INVENTION

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting specific nucleic acid sequences in a biological sample is nucleic acid sequencing.

Nucleic acid sequencing methodology has evolved significantly from the chemical degradation methods used by Maxam and Gilbert and the strand elongation methods used by Sanger. Several sequencing methodologies are now in use which allow for the parallel processing of thousands of nucleic acids all on a single chip. Some platforms include bead-based and microarray formats in which silica beads are functionalized with probes depending on the application of such formats in applications including sequencing, genotyping, gene expression profiling.

SUMMARY OF THE INVENTION

Some embodiments include a method of detecting a plurality of target ligands, comprising: (a) obtaining first and second subpopulations of beads, wherein each bead comprises: a capture probe which specifically binds to a target ligand, a first polynucleotide comprising a barcode indicative of the capture probe, and a barcode primer binding site 3' of the barcode, and a second polynucleotide comprising an index and an index primer binding site 3' of the index, wherein the indexes of the first subpopulation are different from the indexes of the second subpopulation; (b) contacting first target ligands to the capture probes of the first subpopulation of beads, and contacting second target ligands to the capture probes of the second subpopulation of beads; (c) distributing the first and second subpopulations of beads comprising the specifically bound first and second target ligands on a substrate; (d) detecting the capture probes specifically bound to the first and second target ligands; and (e) decoding the locations of beads comprising the detected capture probes on the substrate.

In some embodiments, the capture probe comprises a nucleic acid, the first and second target ligands comprise nucleic acids, and step (d) comprises extending the capture probes specifically bound to the first and second target ligands.

In some embodiments, the first polynucleotide comprises the capture probe.

In some embodiments, the capture probes of the first and the second subpopulations of beads each comprise different nucleotide sequences from one another.

In some embodiments, the different capture probes of the first and second subpopulations of beads comprise the same nucleotide sequences.

In some embodiments, the capture probes comprise a nucleotide sequence capable of hybridizing to a single nucleotide polymorphism (SNP) or complement thereof.

In some embodiments, step (d) comprises polymerase extension of the capture probes.

In some embodiments, step (d) comprises ligase extension of the capture probes.

In some embodiments, step (d) comprises single nucleotide extension of the capture probes.

In some embodiments, step (d) comprises extension of the capture probes with a plurality of nucleotides.

In some embodiments, the extended capture probes comprise a detectable label.

In some embodiments, the capture probe comprises an antibody or antigen binding fragment thereof.

In some embodiments, the capture probes of the first and the second subpopulations of beads each specifically bind to different target ligands from one another.

In some embodiments, the different capture probes of the first and second subpopulations of beads specifically bind to the same target ligands.

In some embodiments, the detecting comprises contacting the first and second target ligands specifically bound to the capture probes with a secondary antibody or antigen-binding fragment thereof, wherein the secondary antibody or antigen-binding fragment thereof comprises a detectable label.

In some embodiments, the barcode primer binding sites comprise the same nucleotide sequence.

In some embodiments, the nucleotide sequences of the indexes of the first subpopulation of beads comprise the same nucleotide sequence, and the nucleotide sequences of the indexes of the second subpopulation of beads comprise the same nucleotide sequence.

In some embodiments, the nucleotide sequences of the index primer binding sites comprise the same nucleotide sequence.

In some embodiments, the contacting first target ligand to the capture probes of the first subpopulation of beads, and the contacting second target ligands to the capture probes of the second subpopulation of beads are performed in different reaction volumes.

Some embodiments also include combining the first and second subpopulations of beads prior to distributing the first and second subpopulations of beads on the substrate.

In some embodiments, the first subpopulation of beads is distributed on the substrate before the second subpopulation of beads is distributed on the substrate.

In some embodiments, step (d) is performed prior to step (c).

In some embodiments, the detected capture probes comprise a detectable marker.

In some embodiments, step (d) further comprises determining the location of the detected capture probes on the substrate.

In some embodiments, determining the location of the detected capture probes comprises at least one cycle of sequencing by synthesis.

In some embodiments, step (e) comprises decoding the location of the indexes of the beads comprising a detected capture probe by sequencing the indexes on the substrate.

In some embodiments, step (e) comprises decoding the location of the barcodes of the beads comprising a detected capture probe by sequencing the barcodes on the substrate.

In some embodiments, a flowcell comprises the substrate.

In some embodiments, the distributed first and second subpopulations of beads comprise an array.

In some embodiments, the first and second target ligands are obtained from different subjects.

In some embodiments, the first and second subpopulations of beads each comprises at least 50 capture probes different from one another.

Some embodiments also include at least 10 different subpopulations of beads, each subpopulation comprising an index different from another subpopulation.

Some embodiments include a method of detecting a target nucleic acid, comprising: (a) obtaining a target nucleic acid comprising a first portion capable of hybridizing to a first capture probe, and a second portion capable of hybridizing to a second capture probe; (b) obtaining a population of beads, each bead comprising: the first capture probe, the second capture probe, wherein the second capture probe is attached to the bead via a cleavable linker, and wherein the second capture probe comprises a detectable label, and a first polynucleotide comprising a barcode indicative of the first or second capture probe, and a barcode primer binding site 3' of the barcode; (c) ligating the first capture probe to the second capture probe, comprising: hybridizing the target nucleic acid to the first and second capture probes of a bead of the population of beads to generate a double-stranded nucleic acid comprising a single-stranded gap between the first and second capture probes, and filing-in the gap between the first and second capture probes; (d) cleaving the cleavable linker to generate a first capture probe comprising the detectable label; (e) distributing the population of beads on a substrate; and (f) decoding the location of the bead comprising the first capture probe comprising the detectable label on the substrate.

In some embodiments, the first capture probe comprises the first polynucleotide.

In some embodiments, step (e) is performed before step (d).

In some embodiments, each bead comprises a second polynucleotide comprising an index indicative of the source of the target nucleic acid, and an index primer binding site 3' of the index.

In some embodiments, step (f) comprises determining the location of the first capture probe comprising the detectable label on the substrate.

In some embodiments, step (f) comprises decoding the location of the barcode of the bead comprising the first capture probe comprising the detectable label on the substrate by sequencing the barcode on the substrate.

In some embodiments, a flowcell comprises the substrate.

In some embodiments, the distributed population of beads comprise an array.

In some embodiments, the population of beads comprises first and second subpopulations of beads, each bead comprising a second polynucleotide comprising an index and an index primer binding site 3' of the index, wherein the indexes of the first subpopulation are different from the indexes of the second subpopulation.

In some embodiments, the nucleotide sequences of the indexes of the first subpopulation of beads comprise the same nucleotide sequence, and the nucleotide sequences of the indexes of the second subpopulation of beads comprise the same nucleotide sequence.

In some embodiments, the ligating or cleaving step with the first subpopulation of beads is performed in a different reaction volume from the ligating or cleaving step with the second subpopulation of beads.

Some embodiments also include combining the first and second subpopulations of beads prior to distributing the population of beads on the substrate.

In some embodiments, the first subpopulation of beads is distributed on the substrate before the second subpopulation of beads is distributed on the substrate.

In some embodiments, step (f) comprises decoding the location of the indexes of the beads comprising a detected capture probe by sequencing the indexes on the substrate.

Some embodiments include a kit comprising: a first and a second subpopulation of beads, wherein each bead comprises: a capture probe which specifically binds to a target ligand, a first polynucleotide comprising a barcode indicative of the capture probe, and a barcode primer binding site 3' of the barcode, and a second polynucleotide comprising an index and an index primer binding site 3' of the index, wherein the indexes of the first subpopulation are different from the indexes of the second subpopulation, wherein a first volume comprises the first subpopulation of beads, and a second volume comprises the second subpopulation of beads.

In some embodiments, the capture probe is selected from a nucleic acid, an antibody or antigen binding fragment thereof.

In some embodiments, the first polynucleotide comprises the capture probe.

In some embodiments, the capture probes of the first and the second subpopulations of beads each specifically bind to different target ligands from one another.

In some embodiments, the different capture probes of the first and second subpopulations of beads specifically bind to the same target ligands.

Some embodiments include a method for decoding the locations of polynucleotides in an array comprising: (a) obtaining a substrate having an array of polynucleotides distributed on a surface of the substrate, wherein each polynucleotide comprises a primer binding site 3' of a barcode, wherein each polynucleotide is linked to a capture probe; (b) hybridizing a plurality of primers to the primer binding sites; and (c) determining the sequences of the barcodes by extending the hybridized primers, wherein the sequence of each barcode is indicative of the location of a polynucleotide in the array.

DETAILED DESCRIPTION

Figure 1:
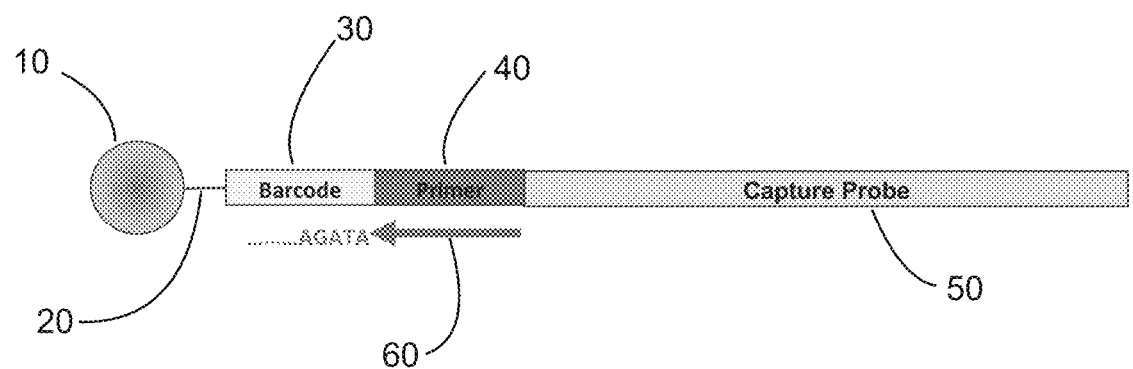
FIG. 1 depicts an example embodiment of a polynucleotide comprising a barcode, primer binding site, and capture probe attached to a bead via a 5' linker.

Some embodiments provided herein include methods and compositions for the detection of target ligands on an array. In some embodiments, a target ligand can include a nucleic acid, a protein, or other antigen. In some embodiments, a capture probe specifically binds to a target ligand from a sample, the location of a bead comprising the capture probe in an array is determined, and the bead is decoded to identify the capture probe and the sample. In some embodiments, a barcode is indicative of a capture probe attached to a bead; and an index is indicative of a subpopulation of beads. In some embodiments, the barcode and the index are determined by sequencing. Some embodiments also include a dual probe assay in which first and second capture probes attached to a bead are ligated together in the presence of a target nucleic acid, an end of the ligation product is cleaved from the bead, and the bead comprising the extended capture probe detected and decoded on an array.

Some embodiments provided herein in relate to high-throughput genotyping on arrays. Some embodiments relate to decoding the locations of microfeatures in an array. In some embodiments, microfeatures comprise polynucleotides having barcodes and indexes. Some embodiments include sequencing barcodes and indexes to identify the locations of polynucleotides in an array.

Decoding by hybridization includes identifying the location of a capture probe in a randomly distributed array of capture probes. The method typically involves several successive cycles of hybridizing labeled hybridization probes to one or more portion of the capture probe, imaging hybridization events, and removing the hybridization probes. Decoding by hybridization requires specialized reagents, specialized fluidic devices and specialized detectors. In some embodiments, decoding by hybridization can take up to 8 hours with 7-8 successive cycles.

Embodiments of the invention include random-distributed arrays of polynucleotides comprising a primer binding site and a barcode. In some embodiments, the barcode can be readily sequenced to decode the array using a high throughput sequencing system. Some embodiments can significantly reduce the time taken to decode an array with no additional reagents, hybridization probes, or specialized decoding equipment.

Some embodiments include the use of next generation sequencing (NGS) techniques and bead-based microarrays. Some such embodiments deliver high-performance, low-cost and high throughput genotyping assays that can be run on a generic NGS sequencing platform with minor modifications to substrates and reagents.

In some multiplexing methods, multiple nucleic samples from different sources can be processed in parallel by keeping each sample physically separated. Some embodiments provided herein include a nucleic acid indexing method that removes the need for physical barriers separating individual samples in all steps by indexing each sample via an index on an associated bead. In some embodiments, index demultiplexing is performed by sequencing and can be executed at a customer site using standard sequencing by synthesis (SBS) chemistry. In addition, cost, space and time limitations due to internal decoding of a beadarray are reduced by adopting a decode by sequencing (DBS) approach that can be implemented at the customer site using a standard platform and SBS chemistry.

Figure 5A:
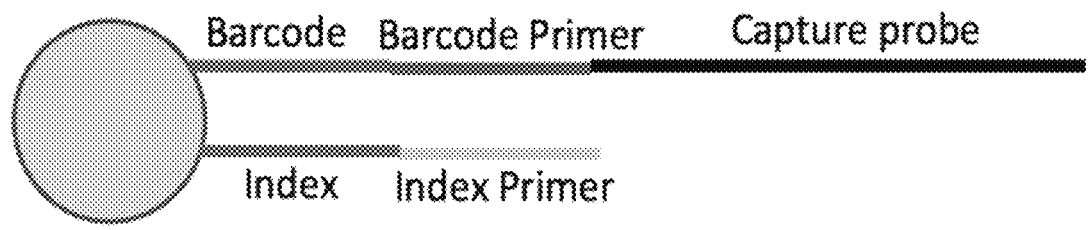
FIG. 5A depicts an example embodiment of a bead with an attached first polynucleotide comprising a barcode, a barcode primer binding site, and a capture probe, and with an attached second polynucleotide comprising an index and an index primer binding site.

Some embodiments include an indexed enrichment bead-pool comprising a bead depicted in FIG. 5A. In some such embodiments, a bead includes a first polynucleotide comprising a locus-specific capture probe, a barcode for positional identification of the associated probe on an array, and a barcode primer binding site for SBS reading of the barcode; and a second polynucleotide comprising an index for sample multiplexing, and an index primer binding site for SBS reading of the index.

In some embodiments, a beadpool complexity is defined by the number of capture probes, or plexity (N) and by the number of samples supported (S). Thus, a beadpool supporting plexity N and S samples will consist of S×N unique bead types. In some embodiments, capture probes and/or index primers include additional 3' orthogonal blockers to avoid interference during SBS on one of the two oligonucleotides.

Some embodiments include conducting a genotyping assay in which a multiwell plate containing S wells is loaded with S beadpools, each beadpool having a unique sample index, with each well containing N unique bead types. After nucleic acid library generation from samples, such treating a nucleic acid sample with steps including random primer amplification followed by enzymatic fragmentation and clean up, each sample library is added to an indexed well and allowed to hybridize to the capture probes. After hybridization is complete, a single base extension assay to probe the SNP of interest is executed by adding an incorporation mix that includes fluorescent nucleotides and an appropriate polymerase. At the end of the incorporation, all bead-capture samples in a plate are pooled and loaded into a flowcell. The flowcell can be plain or patterned, and the surface appropriately modified to support the immobilization of beads at the desired density. In some embodiments, upon bead immobilization, a SNP readout is performed which includes a single scan cycle to read the signal deriving from fluorescent incorporation at the SNP site. This cycle may include an SBS cycle on the instrument. A barcode readout is also performed which includes 12-20 SBS cycles, depending on beadpool plexity, to identify capture probe and position of a specific bead within the flowcell. In some embodiments, this step could be replaced by additional cycles of sequencing past the identified SNP. A sample index readout is also performed which includes 6-12 SBS cycles to read the sample index. In some embodiments, the entire on-flowcell assay can include less than about 30 SBS cycles and can be executed in less than 4 hours.

As used herein, "array" can refer to a population of different microfeatures, such as microfeatures comprising polynucleotides, which are associated or attached with a surface such that the different microfeatures can be differentiated from each other according to relative location. An individual feature of an array can include a single copy of a microfeature or multiple copies of the microfeature can be present as a population of microfeatures at an individual feature of the array. The population of microfeatures at each feature typically is homogenous, having a single species of microfeature. Thus, multiple copies of a single nucleic acid sequence can be present at a feature, for example, on multiple nucleic acid molecules having the same sequence.

In some embodiments, a heterogeneous population of microfeatures can be present at a feature. Thus, a feature may but need not include only a single microfeature species and can instead contain a plurality of different microfeature species such as a mixture of nucleic acids having different sequences. Neighboring features of an array can be discrete one from the other in that they do not overlap. Accordingly, the features can be adjacent to each other or separated by a gap. In embodiments where features are spaced apart, neighboring sites can be separated, for example, by a distance of less than 100 µm, 50 µm, 10 µm, 5 µm, 1 µm, 0.5 µm, 100 nm, 50 nm, 10 nm, 5 nm, 1 nm, 0.5 nm, 100 pm, 50 pm, 1 pm or any distance within a range of any two of the foregoing distances. The layout of features on an array can also be understood in terms of center-to-center distances between neighboring features. An array useful in the invention can have neighboring features with center-to-center spacing of less than about 100 µm, 50 µm, 10 µm, 5 µm, 1 µm, 0.5 µm, 100 nm, 50 nm, 10 nm, 5 nm, 1 nm, 0.5 nm, 100 pm, 50 pm, 1 pm or any distance within a range of any two of the foregoing distances.

In some embodiments, the distance values described above and elsewhere herein can represent an average distance between neighboring features of an array. As such, not all neighboring features need to fall in the specified range unless specifically indicated to the contrary, for example, by a specific statement that the distance constitutes a threshold distance between all neighboring features of an array. Embodiments can be used with arrays having features at any of a variety of densities. Examples ranges of densities for certain embodiments include from about 10,000,000 features/cm$^2$ to about 2,000,000,000 features/cm$^2$; from about 100,000,000 features/cm$^2$ to about 1,000,000,000 features/cm$^2$; from about 100,000 features/cm$^2$ to about 10,000,000 features/cm$^2$; from about 1,000,000 features/cm$^2$ to about 5,000,000 features/cm$^2$; from about 10,000 features/cm$^2$ to about 100,000 features/cm$^2$; from about 20,000 features/cm$^2$ to about 50,000 features/cm$^2$; from about 1,000 features/cm$^2$ to about 5,000 features/cm$^2$, or any density within a range of any two of the foregoing densities.

As used herein, "surface" can refer to a part of a substrate or support structure that is accessible to contact with reagents, beads or analytes. The surface can be substantially flat or planar. Alternatively, the surface can be rounded or contoured. Example contours that can be included on a surface are wells, depressions, pillars, ridges, channels or the like. Example materials that can be used as a substrate or support structure include glass such as modified or functionalized glass; plastic such as acrylic, polystyrene or a copolymer of styrene and another material, polypropylene, polyethylene, polybutylene, polyurethane or TEFLON; polysaccharides or cross-linked polysaccharides such as agarose or Sepharose; nylon; nitrocellulose; resin; silica or silica-based materials including silicon and modified silicon; carbon-fibre; metal; inorganic glass; optical fibre bundle, or a variety of other polymers. A single material or mixture of several different materials can form a surface useful in the invention. In some embodiments, a surface comprises wells. In some embodiments, a support structure can include one or more layers. Example support structures can include a chip, a film, a multi-well plate, and a flow-cell.

As used herein, "bead" can refer to a small body made of a rigid or semi-rigid material. The body can have a shape characterized, for example, as a sphere, oval, microsphere, or other recognized particle shape whether having regular or irregular dimensions. Example materials that are useful for beads include glass such as modified or functionalized glass; plastic such as acrylic, polystyrene or a copolymer of styrene and another material, polypropylene, polyethylene, polybutylene, polyurethane or TEFLON; polysaccharides or cross-linked polysaccharides such as agarose or Sepharose; nylon; nitrocellulose; resin; silica or silica-based materials including silicon and modified silicon; carbon-fiber; metal; inorganic glass; or a variety of other polymers. Example beads include controlled pore glass beads, paramagnetic beads, thoria sol, Sepharose beads, nanocrystals and others known in the art. Beads can be made of biological or non-biological materials. Magnetic beads are particularly useful due to the ease of manipulation of magnetic beads using magnets at various steps of the methods described herein. Beads used in certain embodiments can have a diameter, width or length from about 0.1 µm to about 100 µm, from about 0.1 nm to about 500 nm. In some embodiments, beads used in certain embodiments can have a diameter, width or length less than about 100 μm, 50 μm, 10 μm, 5 μm, 1 μm, 0.5 μm, 100 nm, 50 nm, 10 nm, 5 nm, 1 nm, 0.5 nm, 100 pm, 50 pm, 1 pm or any diameter, width or length within a range of any two of the foregoing diameters, widths or lengths. Bead size can be selected to have reduced size, and hence get more features per unit area, whilst maintaining sufficient signal (template copies per feature) in order to analyze the features.

In some embodiments, polynucleotides can be attached to beads. In some embodiments, the beads can be distributed into wells on the surface of a substrate. Example bead arrays that can be used in certain embodiments include randomly ordered BEADARRAY technology (Illumina Inc., San Diego Calif.). Such bead arrays are disclosed in Michael et al., Anal Chem 70, 1242-8 (1998); Walt, Science 287, 451-2 (2000); Fan et al., Cold Spring Harb Symp Quant Biol 68:69-78 (2003); Gunderson et al., Nat Genet 37:549-54 (2005); Bibikova et al. Am J Pathol 165:1799-807 (2004); Fan et al., Genome Res 14:878-85 (2004); Kuhn et al., Genome Res 14:2347-56 (2004); Yeakley et al., Nat Biotechnol 20:353-8 (2002); and Bibikova et al., Genome Res 16:383-93 (2006), each of which is incorporated by reference in its entirety.

As used herein "polynucleotide" and "nucleic acid", may be used interchangeably, and can refer to a polymeric form of nucleotides of any length, either ribonucleotides or deoxyribonucleotides. Thus, this term includes single-, double-, or multi-stranded DNA or RNA. The term polynucleotide also refers to both double and single-stranded molecules. Examples of polynucleotides include a gene or gene fragment, genomic DNA, genomic DNA fragment, exon, intron, messenger RNA (mRNA), transfer RNA, ribosomal RNA, non-coding RNA (ncRNA) such as PIWI-interacting RNA (piRNA), small interfering RNA (siRNA), and long non-coding RNA (lncRNA), small hairpin (shRNA), small nuclear RNA (snRNA), micro RNA (miRNA), small nucleolar RNA (snoRNA) and viral RNA, ribozyme, cDNA, recombinant polynucleotide, branched polynucleotide, plasmid, vector, isolated DNA of any sequence, isolated RNA of any sequence, nucleic acid probe, primer or amplified copy of any of the foregoing. A polynucleotide can include modified nucleotides, such as methylated nucleotides and nucleotide analogs including nucleotides with non-natural bases, nucleotides with modified natural bases such as aza- or deaza-purines. A polynucleotide can be composed of a specific sequence of four nucleotide bases: adenine (A); cytosine (C); guanine (G); and thymine (T). Uracil (U) can also be present, for example, as a natural replacement for thymine when the polynucleotide is RNA. Uracil can also be used in DNA. Thus, the term 'sequence' refers to the alphabetical representation of a polynucleotide or any nucleic acid molecule, including natural and non-natural bases.

As used herein, "target nucleic acid" or grammatical equivalent thereof can refer to nucleic acid molecules or sequences that it is desired to sequence, analyze and/or further manipulate. In some embodiments, a target nucleic acid can be attached to an array. In some embodiments, a capture probe can be attached to an array and the array used subsequently to detect a target nucleic acid in a sample that interacts with the probe. In this regard, it will be understood that in some embodiments, the terms "target" and "probe" can be used interchangeably with regard to nucleic acid detection methods.

As used herein, "capture probe" can refer to a polynucleotide having sufficient complementarity to specifically hybridize to a target nucleic acid. A capture probe can function as an affinity binding molecule for isolation of a target nucleic acid from other nucleic acids and/or components in a mixture. In some embodiments, a target nucleic acid can be specifically bound by a capture probe through intervening molecules. Examples of intervening molecules include linkers, adapters and other bridging nucleic acids having sufficient complementarity to specifically hybridize to both a target sequence and a capture probe.

As used herein, "hybridization", "hybridizing" or grammatical equivalent thereof, can refer to a reaction in which one or more polynucleotides react to form a complex that is formed at least in part via hydrogen bonding between the bases of the nucleotide residues. The hydrogen bonding can occur by Watson-Crick base pairing, Hoogstein binding, or in any other sequence-specific manner. The complex can have two strands forming a duplex structure, three or more strands forming a multi-stranded complex, a single self-hybridizing strand, or any combination of thereof. The strands can also be cross-linked or otherwise joined by forces in addition to hydrogen bonding.

As used herein, "extending", "extension" or any grammatical equivalents thereof can refer to the addition of dNTPs to a primer, polynucleotide or other nucleic acid molecule by an extension enzyme such as a polymerase. For example, in some methods disclosed herein, the resulting extended primer includes sequence information of an RNA. While some embodiments are discussed as performing extension using a polymerase such as a DNA polymerase, or a reverse transcriptase, extension can be performed in any other manner well known in the art. For example, extension can be performed by ligating short pieces of random oligonucleotides together, such as oligonucleotides that have hybridized to a strand of interest.

As used herein, "ligation" or "ligating" or other grammatical equivalents thereof can refer to the joining of two nucleotide strands by a phosphodiester bond. Such a reaction can be catalyzed by a ligase. A ligase refers to a class of enzymes that catalyzes this reaction with the hydrolysis of ATP or a similar triphosphate.

Decoding by Sequencing

Embodiments include decoding the location of microfeatures of an array using high throughput sequencing. In some embodiments, the microfeatures of an array comprise polynucleotides. In some embodiments, the polynucleotides can be randomly distributed on the surface of the substrate. In some embodiments, a polynucleotide can include a primer binding site, and a barcode. In some embodiments, a polynucleotide can include a capture probe, a primer binding site, and a barcode.

Some embodiments to decode the location of polynucleotides in an array can include (a) obtaining a substrate having an array of polynucleotides distributed on a surface of the substrate, wherein each polynucleotide comprises a barcode and a primer binding site; (b) hybridizing a plurality of primers to the primer binding sites; and (c) determining the sequences of the barcodes by extending the hybridized primers. In some such embodiments, the sequence of each barcode can indicate the location of a polynucleotide in the array. For example, in some embodiments an array can be prepared with polynucleotides in which the barcodes are known to be associated with certain capture probes, such that identifying the location of a barcode on an array, can indicate the location of the associated capture probe. In such embodiments, each polynucleotide can be associated with a capture probe through a common element. For example, a polynucleotide and a capture probe can each be bound to the same microfeature, such as a bead. In more such embodiments, each polynucleotide can include a capture probe.

In some embodiments, a barcode can include a nucleic acid sequence that can be used to identify a polynucleotide within an array. The barcode can include a unique nucleotide sequence that is distinguishable from other barcodes. It can also be distinguishable from other nucleotide sequences within the polynucleotides and target nucleic acids by the barcode's sequence, and also by the barcode's location within the polynucleotide, for example by its location 5' of the primer binding site. For example, in some embodiments, the sequence of a barcode may be present more than once in plurality of nucleic acids, however, the barcode which is located 5' of the primer binding site can be detected. A barcode can be of any desired sequence length sufficient to be unique nucleotide sequence within a plurality of barcodes in a population and/or within a plurality of polynucleotides and target nucleic acids that are being analyzed or interrogated. In some embodiments, a barcode is a nucleic acid or region within a polynucleotide ranging from about 6-30 nucleotides. A barcode can be, for example, 6, 7, 8, 9, 10, 11, 12, 13, 14, 15, 16, 17, 18, 19, 20, 21, 22, 23, 24, 25, 26, 27, 28, 29 or 30 nucleotides, or longer. For example, a barcode can be 35, 40, 45 or 50 nucleotides or longer. Suitable barcodes for some embodiments are disclosed in of U.S. Pat. No. 8,053,192, which is incorporated by reference in its entirety. In some embodiments, a barcode can distinguish a polynucleotide from another polynucleotide in an array, such that each barcode is different from another barcode. In some embodiments, a barcode can distinguish a population of polynucleotides from another population of polynucleotides in an array, such that a set of barcodes is different from another set of barcodes.

In some embodiments, the primer binding site can be 3' of the barcode such that a primer hybridized to the primer binding site can be extended to provide the complement of the barcode. For example, the primer can be extended to obtain the sequence of the barcode. In some embodiments, the primer binding site can be directly adjacent to the barcode in a polynucleotide. In some embodiments, each primer binding site in a population of polynucleotides can have the same sequence. In some embodiments, a subpopulation of polynucleotides can include a primer binding sites with a first sequence, and another subpopulation of polynucleotides can include primer binding sites with a second sequence. In some embodiments, hybridizing different primers to a plurality of different primer binding sites can be simultaneous, sequential, or iterative.

Some embodiments include polynucleotides comprising a capture probe. In some embodiments, the capture probe can include a sequence that can hybridize to a target nucleic acid. In some embodiments, a population of polynucleotides can include capture probes that are different from one another. In some embodiments, each capture probe can be different from one another. In some embodiments, the capture probes can be similar to one another, for example they can have similar sequences, and/or similar sequences with similar lengths. In some embodiments, a capture probe can differ from one another capture probe by a number of less than 20, 19, 18, 17, 16, 15, 14, 13, 12, 11, 10, 9, 8, 7, 6, 5, 4, 3, or 2 nucleotides, in which the number of nucleotides can be consecutive nucleotides, non-consecutive nucleotides, inserted nucleotides, or deleted nucleotides in a capture probe. In some embodiments a capture probe can differ from one another capture probe by a single nucleotide. In some embodiments, the primer binding site and barcode can be 5' of the capture probe. In some embodiments, the primer binding site and barcode can be 3' of the capture probe.

Some embodiments include polynucleotides comprising cleavable linkers. In some such embodiments, the cleavable linker can be located such that cleaving the linker can separate the capture probe from the primer binding site and the barcode. In some embodiments, the cleavable linker can be located within the polynucleotide between the capture probe, and the primer binding site and the barcode. In some embodiments, a cleavable linker can remove the polynucleotide comprising the primer binding site and the barcode linked to a capture probe. For example, the polynucleotide and capture probe can both be bound to a bead. Cleavage of the cleavable linker can remove the polynucleotide comprising the primer binding site and the barcode from the bead.

In some embodiments, a cleavable linker can have a length corresponding to at least 2, 3, 5, 10, 15, 20, 25, 30, 50, 100, 500 nucleotides, or a length within a range of any two of the foregoing lengths. In some embodiments, a cleavable linker is susceptible to cleavage with agents such as light, base, acid and enzymes such as sequence specific restriction enzymes or proteases. A cleavable linker can include a certain sequence of nucleotides, such as the recognition site of an enzyme, and/or can include certain modified nucleotides susceptible to cleavage with an agent. In some embodiments, a cleavable linker can include uracil, which is cleavable by an exogenous base cleaving agent such as DNA glycosylase (UDG). In some embodiments, a cleavable linker can include 8-hydroxyguanine which can be cleaved by 8-hydroxyguanine DNA glycosylase (FPG protein). More examples of cleavable linkers are disclosed in in U.S. Pat. App. Pub. 2005/0181394, which is incorporated by reference in its entirety.

In some embodiments, the polynucleotides are attached to a substrate. In some embodiments, a substrate can include a bead. Polynucleotides can be immobilized to a substrate, such as bead or other surface by single point covalent attachment to the surface of the substrate at or near the 5' end or the 3' end of the polynucleotide. In some embodiments, a polynucleotide can include a spacer which is attached to the substrate. In some embodiments, a spacer can have a length corresponding to at least 2, 3, 5, 10, 15, 20, 25, 30, 50, 100, 500 nucleotides, or a length within a range of any two of the foregoing lengths. Any suitable covalent attachment means known in the art may be used for this purpose. The chosen attachment chemistry will depend on the nature of the solid support, and any derivatization or functionalization applied to it. The polynucleotide may include a moiety, which may be a non-nucleotide chemical modification, to facilitate attachment. In some embodiments, the polynucleotide may include a sulfur-containing nucleophile, such as phosphorothioate or thiophosphate, for example, located at the 5' end. In the case of solid-supported polyacrylamide hydrogels, this nucleophile will bind to a bromoacetamide group present in the hydrogel. An example means of attaching polynucleotide to a solid support is via 5' phosphorothioate attachment to a hydrogel comprised of polymerized acrylamide and N-(5-bromoacetamidylpentyl) acrylamide (BRAPA), which is disclosed in U.S. Pat. No. 8,168,388 which is incorporated by reference in its entirety.

In some embodiments, the location of polynucleotides in the array can be decoded by sequencing barcodes of the polynucleotides. For example, a sequence of a barcode can be associated with a site on an array, and the site can be associated with a particular capture probe. Some embodiments include Next Generation Sequencing (NGS) which can refer to sequencing methods that allow for massively parallel sequencing of clonally amplified molecules and of single nucleic acid molecules. Examples of NGS include sequencing-by-synthesis (SBS) using reversible dye terminators, and sequencing-by-ligation. In SBS, extension of a nucleic acid primer along a nucleic acid template is monitored to determine the sequence of nucleotides in the template. The underlying chemical process can be polymerization. In a particular polymerase-based SBS embodiment, fluorescently labeled nucleotides are added to extend a primer in a template dependent fashion such that detection of the order and type of nucleotides added to the primer can be used to determine the sequence of the template.

One or more amplified nucleic acids can be subjected to an SBS or other detection technique that involves repeated delivery of reagents in cycles. For example, to initiate a first SBS cycle, one or more labeled nucleotides, DNA polymerase, etc., can be flowed into/through a hydrogel bead that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell before or after detection occurs. Washes can be carried out between the various delivery steps. The cycle can then be repeated n times to extend the primer by n nucleotides, thereby detecting a sequence of length n.

Some SBS embodiments include detection of a proton released upon incorporation of a nucleotide into an extension product. For example, sequencing based on detection of released protons can use an electrical detector and associated techniques that are commercially available. Examples of such sequencing systems are pyrosequencing such as a commercially available platform from 454 Life Sciences a subsidiary of Roche; sequencing using γ-phosphate-labeled nucleotides, such as a commercially available platform from Pacific Biosciences; and sequencing using proton detection, such as a commercially available platform from Ion Torrent subsidiary of Life Technologies. Some embodiments include pyrosequencing which is described in U.S. Pat. App. Pub. 2005/0130173 and 2006/0134633 and U.S. Pat. Nos. 4,971,903; 6,258,568 and 6,210,891 which are each incorporated by reference in its entirety. Some embodiments include sequencing by ligation which is disclosed in U.S. Pat. Nos. 5,599,675; and 5,750,341, each of which is incorporated by reference in its entirety.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero mode waveguides (ZMWs). Another useful sequencing technique is nanopore sequencing. In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore.

As shown in FIG. 1, in some embodiments a microfeature of an array can include a polynucleotide attached to a bead 10 via a 5' linker 20. The polynucleotide can include a bar code 30, a primer binding site 40, and a capture probe 50. A primer 60 can hybridize to the primer binding site and be extended to obtain the sequence of the barcode to decode the location of the microfeature in the array. In some embodiments, the capture probe can hybridize to target nucleic acids and the capture probe can be extended, for example by a polymerase or by a ligase. In some embodiments, the capture probe can participate in bridge amplification. Methods of bridge amplification are disclosed in U.S. Pat. Nos. 7,985,565 and 7,115,400, which are each incorporated by reference in its entirety.

Figure 2:
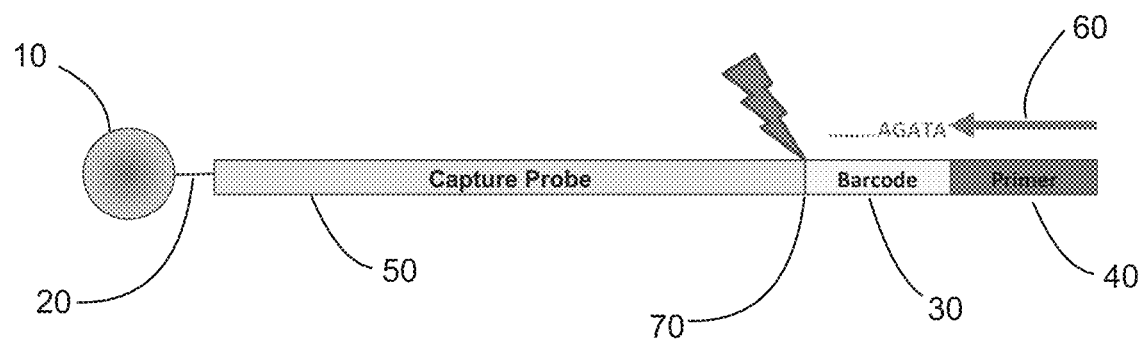
FIG. 2 depicts an example embodiment of a polynucleotide comprising a capture probe, barcode, and primer binding site, attached to a bead via a 5' linker, and having a cleavable linker between the capture probe and barcode.

As shown in FIG. 2, in some embodiments a microfeature of an array can include a polynucleotide comprising a capture probe 50, barcode 30, and primer binding site 40, in which the polynucleotide is attached to a bead 10 via a 5' linker 20. In some embodiments, the polynucleotide can include a cleavable linker 70 between the capture probe and barcode. In some embodiments, a primer 60 can be hybridized to the primer binding site, and the sequence of the barcode determined, thereby decoding the location of the microfeature in the array. In some embodiments, the polynucleotide can be cleaved, and the barcode and primer binding site removed from the microfeature comprising the bead and capture probe. Some such embodiments provide decoded arrays before hybridizing target nucleic acids with the capture probes. In some embodiments, a target nucleic acid can be hybridized to the capture probe at the decoded location in the array. In some embodiments, the hybridized capture probe can be extended, for example by a polymerase or by a ligase. In some embodiments, the capture probe can participate in bridge amplification.

Figure 3:
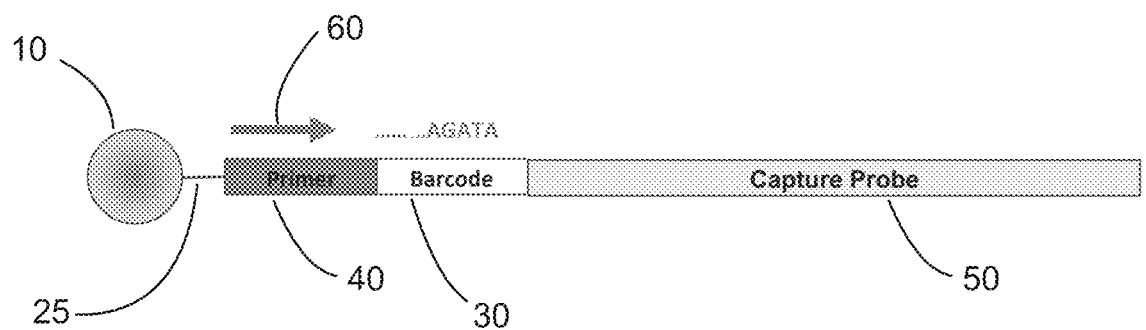
FIG. 3 depicts an example embodiment of a polynucleotide comprising a barcode, primer binding site, and capture probe attached to a bead via a 3' linker.

As shown in FIG. 3, in some embodiments a microfeature of an array can include a polynucleotide comprising a barcode 30, primer binding site 40, and capture probe 50 attached to a bead 10 via a 3' linker 25. In some embodiments, the primer binding site can abut a linker attached to the bead. Some embodiments can include the use of such microfeatures in assays to screen for and develop certain polymerases. For example, the activity of polymerases can be screened for primer sites attached to beads without spacers, compared to primer sites attached to beads with spacers. In some embodiments, a target nucleic acid can be hybridized to the capture probe. In some embodiments, the hybridized target nucleic acids extended, for example by a polymerase or by a ligase.

Figure 4:
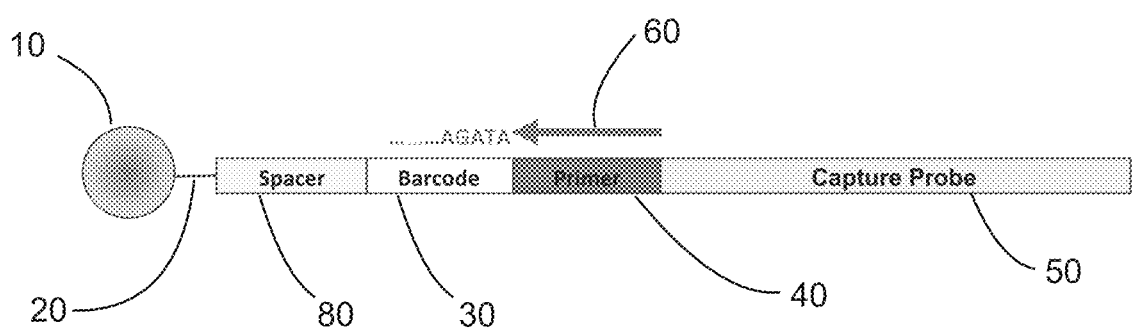
FIG. 4 depicts an example embodiment of a polynucleotide comprising a spacer, barcode, primer binding site, and capture probe attached to a bead via a 5' linker.

As shown in FIG. 4, embodiments of a microfeature of an array can include a polynucleotide comprising a spacer 80, barcode 30, primer binding site 40, and capture probe 50 attached to a bead 10 via a 5' linker 20.

Sequencing Multiple Target Nucleic Acids

Some embodiments include sequencing a plurality of target nucleic acids. In some embodiments, the target nucleic acids can be derived from different sources, such as different subjects, for example genomic DNA from different subjects. In some embodiments, different target nucleic acids can be associated with different indexes, such that an index can identify a particular population of target nucleic acids, such as a population derived from a single source.

Some embodiments include obtaining at least a first and a second subpopulation of beads, wherein each bead comprises a first polynucleotide comprising a capture probe, a barcode indicative of the capture probe of the same bead, and a barcode primer binding site 3' of the barcode, and a second polynucleotide comprising an index and an index primer binding site 3' of the index, wherein the indexes of the first subpopulation are different from the indexes of the second subpopulation.

In some embodiments, the nucleotide sequences of the indexes of the first subpopulation of beads comprise the same nucleotide sequence, and the nucleotide sequences of the indexes of the second subpopulation of beads comprise the same nucleotide sequence. In some embodiments, the nucleotide sequences of the index primer binding sites comprise the same nucleotide sequence.

In some embodiments, the capture probes of the first and/or the second subpopulations of beads each comprise different nucleotide sequences from one another. For example, the capture probes of the first subpopulation can be different from one another; and/or the capture probes of the first subpopulation can be different from one another. In some embodiments, the capture probes of the first subpopulations of beads each comprise capture probes having the same nucleotide sequences as the capture probes of the second subpopulations of beads. In some embodiments, a capture probe can comprise a nucleotide sequence capable of hybridizing to a single nucleotide polymorphism (SNP) or complement thereof. In some embodiments, the barcode primer binding sites comprise the same nucleotide sequence.

Some embodiments also include hybridizing first target nucleic acids to the capture probes of the first subpopulation of beads, and hybridizing second target nucleic acids to the capture probes of the second subpopulation of beads. In some such embodiments, the hybridizing first target nucleic acids to the capture probes of the first subpopulation of beads, and the hybridizing second target nucleic acids to the capture probes of the second subpopulation of beads are performed at different locations. For example, the different locations comprise different reaction volumes, such as different wells, such as different wells in a multiwall plate. For example, in a 96 well plate, 96 different subpopulations of beads could be hybridized with 96 different target nucleic acids, in which each different subpopulation of beads is hybridized to a different target nucleic acid in a different well.

In some embodiments, the different subpopulations of beads comprising the hybridized capture probes and target nucleic acids are distributed on a substrate, such as a planar substrate. In some embodiments, the distributed subpopulations of beads comprise an array. In some embodiments, the substrate comprises a plurality of discrete sites. In some embodiments, the substrate comprises a plurality of wells. In some embodiments, the substrate comprises a plurality of channels. In some embodiments, a flowcell comprises the substrate.

In some embodiments, the different subpopulations of beads comprising the hybridized capture probes and target nucleic acids are combined prior to being distributed on the substrate. In some embodiments, the different subpopulations of beads comprising the hybridized capture probes and target nucleic acids are distributed on the substrate sequentially. For example, a first subpopulation of beads comprising the hybridized capture probes and target nucleic acids is distributed on the substrate before a second subpopulation of beads comprising hybridized capture probes and target nucleic acids is distributed on the substrate.

In some embodiments, the hybridized capture probes are extended. In some embodiments, the hybridized capture probes are extended before the different subpopulations of beads comprising the hybridized capture probes and target nucleic acids are distributed on the substrate. In some embodiments, the hybridized capture probes are extended after the beads comprising the hybridized capture probes and target nucleic acids are distributed on the substrate. In some embodiments, extending the hybridized capture probes can include polymerase extension. In some embodiments, extending the hybridized capture probes can include ligase-based extension, such as ligation of an extension probe to a capture probe in the presence of a ligase. In some embodiments, the extension step can add a detectable marker to the extended capture probe. In some embodiments, the detectable marker can include a fluorescent marker.

Some embodiments include decoding the beads on the substrate. Some embodiments include decoding the beads by identifying the locations of extended capture probes, barcodes, and indexes on the substrate. In some embodiments, the presence of a particular barcode at a location on the substrate is indicative of a particular capture probe at the location. In some embodiments, the presence of a certain index at a location on the substrate is indicative that a target nucleic acid of a certain subpopulation of target nucleic acids is associated with the location on the substrate. In some embodiments, the presence of an extended capture probe at a location on the substrate is indicative of the presence of a certain target nucleic acid in the subpopulations of target nucleic acids. In some embodiments, the identity of a barcode, the identity of an index, and the presence of an extended capture probe at a single location on the surface is indicative of the presence of a specific target nucleic in a specific subpopulation of target nucleic acids.

In some embodiments, decoding the beads on the substrate includes detecting the locations of the hybridized capture probes or the extended capture probes. In some embodiments, detecting the location of the hybridized capture probes or the extended capture probes includes extending the hybridized capture probes with a detectable marker. In some embodiments, detecting the location of the hybridized capture probes or the extended capture probes comprises at least one cycle of sequencing by synthesis.

In some embodiments, decoding the beads on the substrate includes decoding the location of the indexes of the beads comprising an extended capture probe. Some embodiments include hybridizing a plurality of index primers to the index primer sites, and extending the hybridized index primers. In some embodiments, extending the hybridized index primers comprises at least one cycle of sequencing by synthesis. In some embodiments, decoding the location of the indexes of the beads comprises sequencing the indexes on the substrate.

In some embodiments, decoding the beads on the substrate includes decoding the location of the barcodes of the beads comprising an extended capture probe. Some embodiments include hybridizing a plurality of barcode primers to the barcode primer sites, and extending the hybridized barcode primers. In some embodiments, decoding the beads on the substrate includes extending the hybridized barcode primers comprises at least one cycle of sequencing by synthesis. In some embodiments, decoding the beads on the substrate includes decoding the location of the barcodes of the beads comprises sequencing the barcodes on the substrate.

In some embodiments, the first and second subpopulations of beads each comprises at least 50 capture probes comprising different nucleotide sequences. In some embodiments, the first and second subpopulations of beads each comprises at least 100, 200, 300, 400, or 500 or more capture probes comprising different nucleotide sequences. In some embodiments, the first and second subpopulations of beads each comprises at least 5000 capture probes comprising different nucleotide sequences. In some embodiments, the first and second subpopulations of beads each comprises at least 50,000 capture probes comprising different nucleotide sequences.

Some embodiments include at least 10 different subpopulations of beads, each subpopulation comprising an index different from another subpopulation. Some embodiments include at least 100 different subpopulations of beads, each subpopulation comprising an index different from another subpopulation. Some embodiments include at least 1000 different subpopulations of beads, each subpopulation comprising an index different from another subpopulation. Some embodiments include at least 10,000 different subpopulations of beads, each subpopulation comprising an index different from another subpopulation.

Aspects of some embodiments are shown in FIG. 5A-FIG. 5E. As shown in FIG. 5A, a subpopulation of beads includes a bead with an attached first polynucleotide comprising a barcode, a barcode primer binding site, and a capture probe, and with an attached second polynucleotide comprising an index and an index primer binding site. Different subpopulations of beads can include different indexes. Different subpopulations of beads, each subpopulation having a particular index can be distributed into wells of a 96 well plate, such that each well contains a single subpopulation of beads.

Figure 5B:
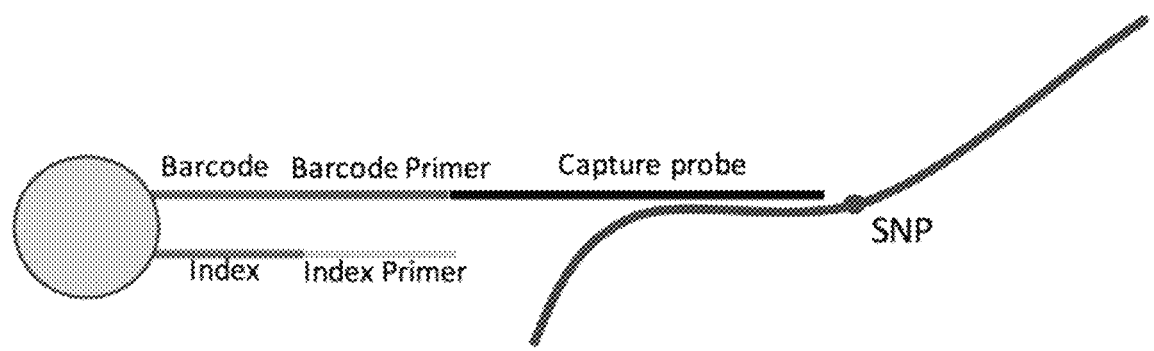
FIG. 5B depicts an example embodiment of a target nucleic containing a single nucleotide polymorphism (SNP) hybridized to a capture probe attached to a bead.

As shown in FIG. 5B, a target nucleic acid from a population of target nucleic acids is hybridized to the capture probe, in which the target nucleic acid contains a SNP. In some embodiments, a subpopulation of target nucleic acids is added to each well containing a subpopulation of beads. Each subpopulation of target nucleic acids can be derived from a different source, such as a different subject. For example, a subpopulation of target nucleic acids can be obtained by preparing a library of nucleic acids from a single source of nucleic acids, such as a single sample of nucleic acids from a subject. In some embodiments, the target nucleic acids do not require an adaptor to be sequenced.

Figure 5C:
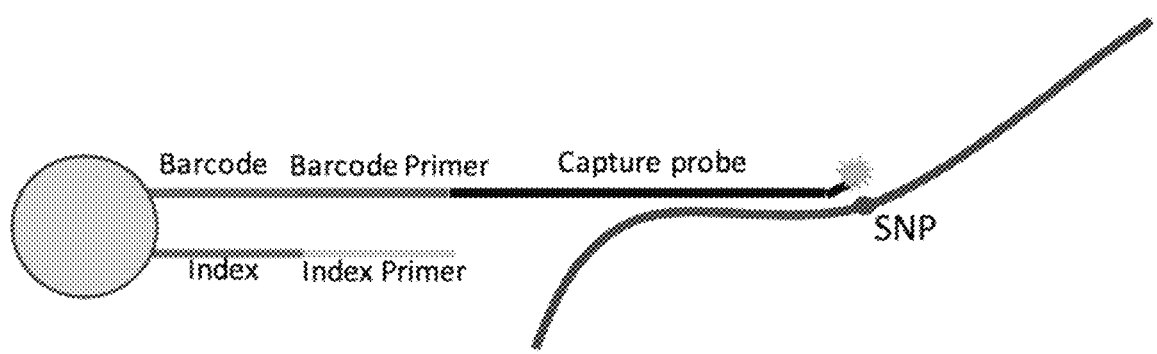
FIG. 5C depicts an example embodiment of capture probe extended with a detectable marker.

As shown in FIG. 5C, a capture probe that is hybridized to a target nucleic acid containing a SNP can be extended. In some embodiments, the extension can be performed by executed by adding an incorporation mix that includes fluorescent nucleotides and an appropriate polymerase. In some embodiments, the extension is a single base extension.

In some embodiments, all beads are combined and distributed on to the surface of a flowcell. The flowcell can have a patterned surface, and the surface can be modified to support the immobilization of beads at a desired density.

In some embodiments, an SNP readout is performed. In some embodiments, a scan cycle is performed to read a signal from incorporation at the SNP site of the capture probe. In some embodiments, this cycle can include at least one cycle of sequence by synthesis. In some embodiments, the 3' ends of the extended capture probes are cleaved and blocked.

Figure 5D:
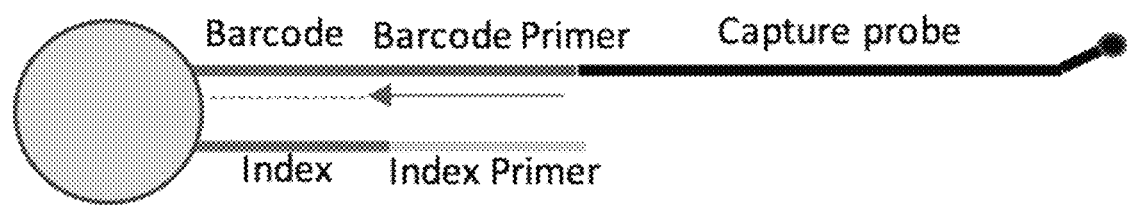
FIG. 5D depicts an example embodiment of a barcode primer hybridized to a barcode primer binding site, and extension of the barcode primer.

As shown in FIG. 5D, a barcode primer is hybridized to the barcode primer binding site, and the barcode primer is extended. In some embodiments, extension of the barcode primer includes a barcode readout. In some embodiments, the extension can include at least one cycle of sequence by synthesis. In some embodiments, the number of cycles of sequence by synthesis can depend of the number of different barcodes in a subpopulation of beads. In some embodiments, the extension can include 12-20 sequence by synthesis cycles. In some embodiments, the extension identifies the capture probe and position of a specific bead within the flowcell.

Figure 5E:
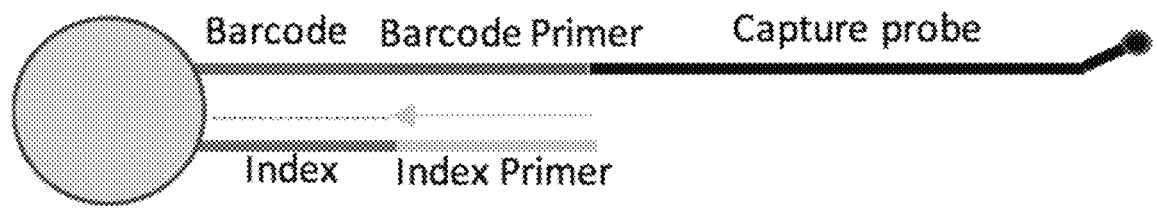
FIG. 5E depicts an example embodiment of an index primer hybridized to an index primer binding site, and extension of the index primer.

As shown in FIG. 5E, an index primer is hybridized to the index primer binding site, and the index primer is extended. In some embodiments, extension of the index primer includes an index readout. In some embodiments, the extension can include at least one cycle of sequence by synthesis. In some embodiments, the number of cycles of sequence by synthesis can depend of the number of different indexes in a plurality of subpopulations of beads. In some embodiments, the extension can include 6-12 sequence by synthesis cycles.

Certain Methods of Detecting Target Ligands

Some embodiments include methods of detecting target ligands. In some embodiments, the target ligands can include nucleic acids, proteins, or other antigens. In some embodiments, the target ligands are obtained from different sources, for example, from different samples, different individual subjects, or different populations of subjects.

In some embodiments, methods of detecting target ligands can include obtaining a population of beads, wherein each bead comprises a capture probe which specifically binds to a target ligand. For example, a capture probe can include a nucleic acid, an antibody, or an antigen-binding fragment of an antibody. In some embodiments, a bead includes a first polynucleotide comprising a barcode indicative of the capture probe of the same bead, and a barcode primer binding site 3' of the barcode. In some embodiments, each bead also includes a second polynucleotide comprising an index and an index primer binding site 3' of the index. In some embodiments, the population of beads includes first and second subpopulations of beads. In some embodiments, the indexes of the first subpopulation of beads are different from the indexes of the second subpopulation of beads. For example, the indexes of the first subpopulation of beads can be used to identify the first subpopulation of beads from the indexes of the second subpopulation of beads.

Some embodiments include contacting first target ligands to the capture probes of the first subpopulation of beads, and contacting second target ligands to the capture probes of the second subpopulation of beads. For example, first target ligands can be obtained from a first sample of ligands, and second target ligands can be obtained from a second sample of ligands. Some embodiments also include distributing the first and second subpopulations of beads comprising the specifically bound first and second target ligands on a substrate. Some embodiments also include detecting the capture probes specifically bound to the first and second target ligands distributed on the substrate. Some embodiments also include decoding the locations of beads comprising the detected capture probes on the substrate.

In some embodiments, the capture probe comprises a nucleic acid and the target ligands comprise nucleic acids. In some embodiments, the first polynucleotide comprises the capture probe. In other embodiments, the capture probe is distinct from the first polynucleotide. In some embodiments, the capture probes of a subpopulation of beads comprises different nucleotide sequences from one another. In some embodiments, different subpopulations of beads can include the same different capture probes. In some embodiments, the capture probes comprise a nucleotide sequence capable of hybridizing to a single nucleotide polymorphism (SNP) or complement thereof.

In some such embodiments, detecting the capture probes specifically bound to the target ligands includes extending the capture probes specifically bound to the target ligands. In some embodiments, the extending can include polymerase extension, and/or ligase extension. In some embodiments the extension include a detectable nucleotide, such as a fluorescently-labeled nucleotide. In some embodiments, the extension include single nucleotide extension of the capture probes. In some embodiments, the extension includes extension of the capture probes with a plurality of nucleotides.

In some such embodiments, the capture probe comprises an antibody or antigen binding fragment thereof. In some embodiments, the capture probes of a subpopulation of beads specifically bind to different target ligands from one another. In some embodiments, different subpopulations of beads can include the same different capture probes. In some such embodiments, the different capture probes of a subpopulation of beads specifically bind to the same target ligands.

In some embodiments, detecting the capture probes specifically bound to the target ligands includes an immunoassay. For example, target ligands specifically bound to the capture probes are contacted with a secondary antibody or antigen-binding fragment thereof, wherein the secondary antibody or antigen-binding fragment thereof comprises a detectable label, such as a fluorescent label.

In some embodiments, the barcode primer binding sites comprise the same nucleotide sequence.

In some embodiments, the nucleotide sequences of the indexes of a subpopulation of beads comprise the same nucleotide sequence and can distinguish a subpopulation of beads from another subpopulation of beads. For example, the nucleotide sequences of the indexes of a first subpopulation of beads, and the nucleotide sequences of the indexes of the second subpopulation of beads comprise the same nucleotide sequence.

In some embodiments, the nucleotide sequences of the index primer binding sites comprise the same nucleotide sequence.

In some embodiments, contacting the first target ligand to the capture probes of the first subpopulation of beads, and contacting the second target ligands to the capture probes of the second subpopulation of beads are performed at different locations. For example, the different locations may comprise different reaction volumes, such as different volumes in different wells of a microtiter plate.

Some embodiments also include combining the first and second subpopulations of beads prior to distributing the first and second subpopulations of beads on the substrate. In other embodiments, the first subpopulation of beads is distributed on the substrate before the second subpopulation of beads is distributed on the substrate. In some embodiments, the subpopulations of beads are distributed on the substrate before the capture probe specifically bound to the ligand is detected.

In some embodiments, detecting the capture probes specifically bound to the target ligands can also include determining the location of the capture probes specifically bound to the target ligands on the substrate.

In some embodiments, decoding the location of the detected capture probes comprises decoding the location of the indexes of the beads comprising a detected capture probe. Some embodiments also include hybridizing a plurality of index primers to the index primer sites, and extending the hybridized index primers. In some embodiments, also include extending the hybridized index primers comprises at least one cycle of sequencing by synthesis. In some embodiments, decoding the location of the indexes of the beads comprises sequencing the indexes on the substrate.

In some embodiments, decoding the location of the detected capture probes comprises decoding the location of the barcodes of the beads comprising a detected capture probe. Some such embodiments include hybridizing a plurality of barcode primers to the barcode primer sites, and extending the hybridized barcode primers. In some embodiments, extending the hybridized barcode primers comprises at least one cycle of sequencing by synthesis. In some embodiments, decoding the location of the barcodes of the beads comprises sequencing the barcodes on the substrate.

In some embodiments, the substrate comprises a plurality of discrete sites. In some embodiments, the substrate comprises a plurality of wells. In some embodiments, the substrate comprises a plurality of channels. In some embodiments, a flowcell comprises the substrate. In some embodiments, the distributed first and second subpopulations of beads comprise an array.

In some embodiments, the first and second subpopulations of beads each comprises at least 50, 100, 500, 1000, or 5000 capture probes different from one another, or any number of capture probes between any two of the foregoing numbers. Some embodiments also include at least 5, 10, 20, 50, 100, 200, 500, 1000 different subpopulations of beads, each subpopulation comprising an index different from another subpopulation, or any number of different subpopulations of beads between any two of the foregoing numbers.

Figure 6A:
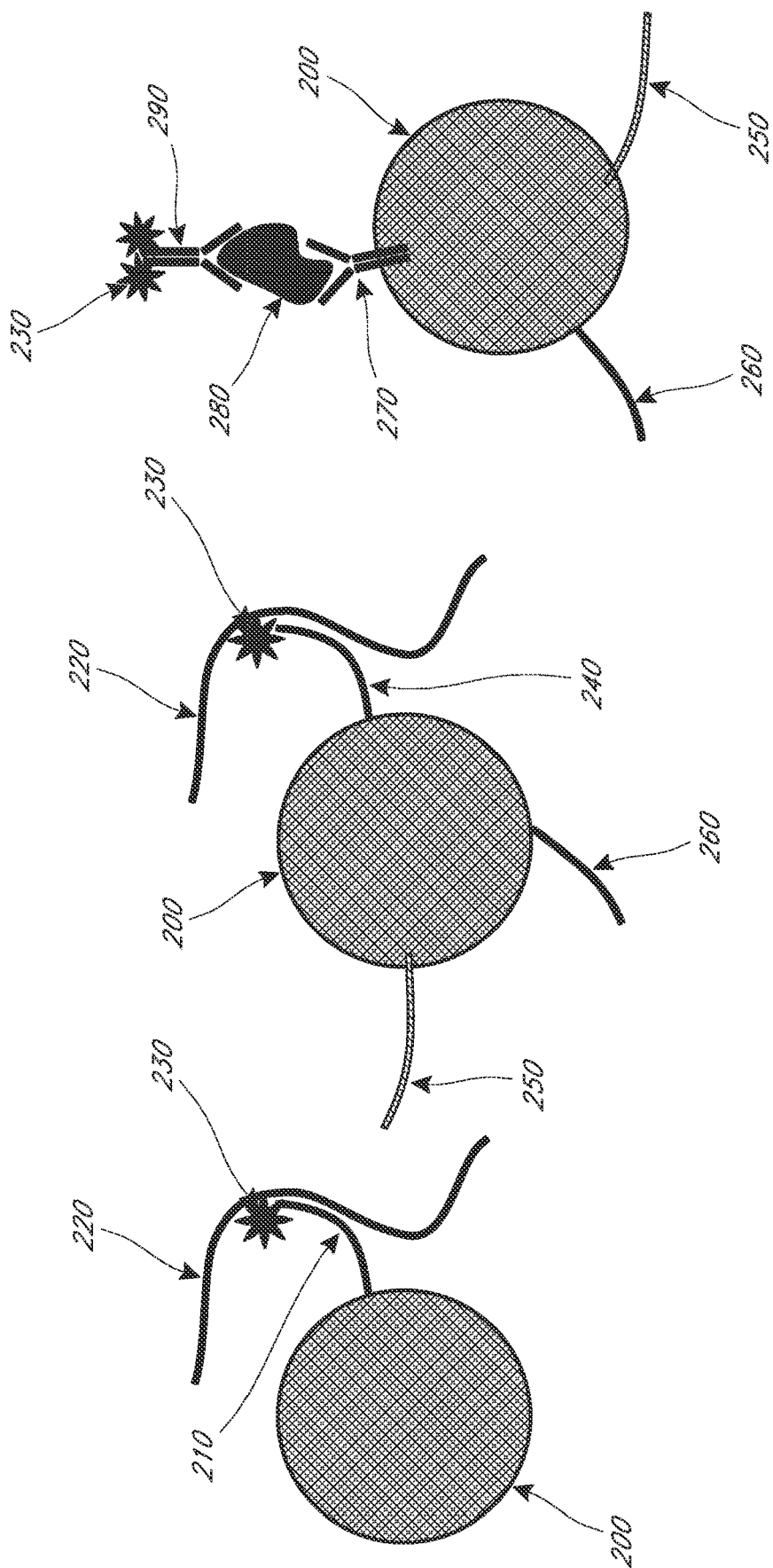
FIG. 6A depicts example embodiment of: a bead comprising a single polynucleotide comprising a capture probe (left panel); a bead comprising a nucleic acid capture probe, a polynucleotide comprising a barcode indicative of the capture probe, and a polynucleotide comprising an index to distinguish a subpopulation of beads from another subpopulation of beads (middle panel); and a bead comprising a capture probe comprising an antibody or antigen-binding fragment of the antibody, a polynucleotide comprising a barcode indicative of the capture probe, and a polynucleotide comprising an index to distinguish a subpopulation of beads from another subpopulation of beads (right panel).

An embodiment is depicted in FIG. 6A, left panel which includes a bead 200 having a polynucleotide 210 attached to the bead. The polynucleotide includes a capture probe which is hybridized to the target nucleic acid 220. The capture probe is extended with a nucleotide comprising a detectable label 230. In some embodiments, the polynucleotide can include a barcode indicative of the capture probe, and a barcode primer binding site useful to sequence and identify the barcode. In some embodiments, the polynucleotide can also include an index indicative of a subpopulation of beads from another subpopulation of beads, and an index primer binding site useful to sequence and identify the index. In some embodiments, the bead can be distributed in an array on a substrate, and decoded. Decoding can include determining the location of the detectable label on the array; determining the barcode attached to the bead on the array; and/or determining the index attached to the bead on the array.

An embodiment is depicted in FIG. 6A, middle panel which includes a bead 200 with a capture probe 240 attached to the bead. The capture probe is hybridized to the target nucleic acid 220. A first polynucleotide 260 comprising a barcode indicative of the capture probe, and a barcode primer binding site useful to sequence and identify the barcode is also attached to the bead. A second polynucleotide 250 comprising an index indicative of a subpopulation of beads from another subpopulation of beads is also attached to the bead. The capture probe is extended with a nucleotide comprising a detectable label 230. In some embodiments, the bead can be distributed in an array on a substrate, and decoded. Decoding can include determining the location of the detectable label on the array; determining the barcode attached to the bead on the array; and/or determining the index attached to the bead on the array.

An embodiment is depicted in FIG. 6A, right panel which includes a bead 200 with a capture probe 270 attached to the bead in which the capture probe is an antibody, or antigen-binding fragment of an antibody. The capture probe is specifically bound to a ligand 280. The ligand is also bound with a secondary antibody 290 which includes a detectable label 230. A first polynucleotide 260 comprising a barcode indicative of the capture probe, and a barcode primer binding site useful to sequence and identify the barcode is also attached to the bead. A second polynucleotide 250 comprising an index indicative of a subpopulation of beads from another subpopulation of beads is also attached to the bead. In some embodiments, the bead can be distributed in an array on a substrate, and decoded. Decoding can include determining the location of the detectable label on the array; determining the barcode attached to the bead on the array; and/or determining the index attached to the bead on the array.

Figure 6B:
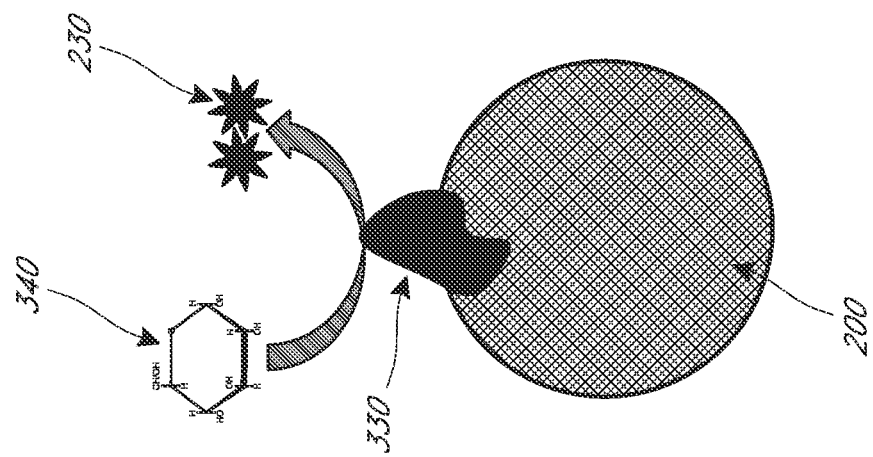
FIG. 6B depicts example embodiments of: a bead comprising first and second capture probes hybridized to a target nucleic acid, in which the first capture probe comprises a cleavable linker (left panel); and a bead comprising a protein capture probe which transiently binds a substrate to generate a signal comprising a detectable label (right panel).
Figure 6B:
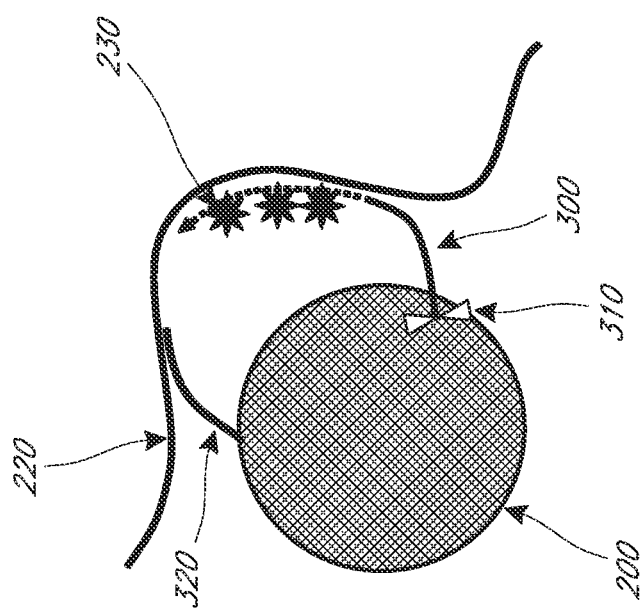

An embodiment is depicted in FIG. 6B, right panel which includes a bead 200 with a capture probe 330 comprising a protein attached to the bead. In some embodiments, the bead can be distributed in an array on a substrate. A substrate 340 for the protein contact the protein to generate a signal comprising a detectable label 230. The location of the signal on the array can be determined. In some embodiments, the bead can include a first polynucleotide comprising a barcode indicative of the capture probe, and a barcode primer binding site useful to sequence and identify the barcode is also attached to the bead. In some embodiments, the bead can include a second polynucleotide comprising an index indicative of a subpopulation of beads from another subpopulation of beads is also attached to the bead. In some embodiments on the bead is decoded on the array. Decoding can include determining the location of the detectable label on the array; determining the barcode attached to the bead on the array; and/or determining the index attached to the bead on the array.

Sequencing and Analysis of Target Nucleic Acids

Some embodiments include sequencing and/or analysis of target nucleic acids. Some embodiments include decoding the locations of polynucleotides in an array according to methods provided herein; hybridizing target nucleic acid to capture probes; extending the capture probes; and detecting the extension of the capture probes hybridized to the target nucleic acid at a location on the array. In some embodiments, the locations of the polynucleotides on an array can be decoded before hybridizing target nucleic acid to the polynucleotides. In some embodiments, the locations of the polynucleotides on an array can be decoded after detecting the extension of the capture probes hybridized to the target nucleic acid. In some such embodiments, each polynucleotide can be associated with a capture probe through a common element. For example, a polynucleotide and a capture probe can each be bound to the same microfeature, such as a bead. In more such embodiments, each polynucleotide can include the capture probe.

Some embodiments include single base extension (SBE) of capture probes. In some embodiments, SBE can be used for detection of an allele, mutations or other features in target nucleic acids. Briefly, SBE utilizes a capture probe that hybridizes to a target genome fragment at a location that is proximal or adjacent to a detection position, the detection position being indicative of a particular locus. A polymerase can be used to extend the 3' end of the capture probe with a nucleotide analog labeled with a detection label. Based on the fidelity of the enzyme, a nucleotide is only incorporated into the capture probe if it is complementary to the detection position in the target nucleic acid. If desired, the nucleotide can be derivatized such that no further extensions can occur using a blocking group, including reversible blocking groups, and thus only a single nucleotide is added. The presence of the labeled nucleotide in the extended capture probe can be detected for example, at a particular location in an array and the added nucleotide identified to determine the identity of the locus or allele. SBE can be carried out under known conditions such as those described in U.S. Pat. Nos. 9,441,267 and 9,045,796 each of which is incorporated by reference in its entirety.

Some embodiments include allele specific primer extension (ASPE). In some embodiments ASPE can include extension of capture probes that differ in nucleotide composition at their 3' end. An ASPE method can be performed using a nucleoside or nucleotide containing a cleavable linker, so that a label can be removed after a probe is detected. This allows further use of the probes or verification that the signal detected was due to the label that has now been removed. Briefly, ASPE can be carried out by hybridizing a target nucleic acid to a capture probe having a 3' sequence portion that is complementary to a detection position and a 5' portion that is complementary to a sequence that is adjacent to the detection position. Template directed modification of the 3' portion of the capture probe, for example, by addition of a labeled nucleotide by a polymerase yields a labeled extension product, but only if the template includes the target sequence. The presence of such a labeled primer-extension product can then be detected, for example, based on its location in an array to indicate the presence of a particular allele. In some embodiments, ASPE can be carried out with multiple capture probes that have similar 5' ends such that they anneal adjacent to the same detection position in a target nucleic acid but different 3' ends, such that only capture probes having a 3' end that complements the detection position are modified by a polymerase. A capture probe having a 3' terminal base that is complementary to a particular detection position is referred to as a perfect match (PM) probe for the position, whereas capture probes that have a 3' terminal mismatch base and are not capable of being extended in an ASPE reaction are mismatch (MM) probes for the position. The presence of the labeled nucleotide in the PM probe can be detected and the 3' sequence of the capture probe determined to identify a particular allele at the detection position.

Some embodiments include methods for decoding the locations of polynucleotides in an array. Some such methods include (a) obtaining a substrate having an array of polynucleotides distributed on a surface of the substrate, wherein each polynucleotide comprises a primer binding site 3' of a barcode, wherein each polynucleotide is linked to a capture probe; (b) hybridizing a plurality of primers to the primer binding sites; and (c) determining the sequences of the barcodes by extending the hybridized primers, wherein the sequence of each barcode is indicative of the location of a polynucleotide in the array. In some embodiments, each polynucleotide is linked to a capture probe via a bead. In some embodiments, each polynucleotide comprises the capture probe. In some embodiments, the capture probe is 3' of the primer binding site. In some embodiments, the capture probe is 5' of the barcode. In some embodiments, a capture probe comprises a different sequence from another capture probe. In some embodiments, a capture probe is different from another capture probe by less than 5 different nucleotides. In some embodiments, each capture probe comprises a different sequence. In some embodiments, the polynucleotides are randomly distributed on the surface of the substrate. In some embodiments, a barcode comprises a different sequence from another barcode. In some embodiments, each barcode comprises a different sequence. In some embodiments, each primer binding site comprises the same sequence. In some embodiments, the polynucleotides are attached to beads. In some embodiments, the beads are distributed in the wells. In some embodiments, each polynucleotide comprises a cleavable linker. In some embodiments, the cleavable linker is adapted to remove the capture probe from the primer binding site and the barcode. In some embodiments, the substrate comprises wells. In some embodiments, each polynucleotide comprises a spacer. In some embodiments, the spacer is attached to the substrate. In some embodiments, the spacer is attached to a bead. Some embodiments also include hybridizing a target nucleic acid to the capture probes. In some embodiments, the hybridizing a target nucleic acid to the capture probes is performed after the determining the sequences of the barcodes. In some embodiments, the hybridizing a target nucleic acid to the capture probes is performed before the determining the sequences of the barcodes. Some embodiments also include extending the hybridized target nucleic acid, or the polynucleotide. In some embodiments, the extending comprises ligation. Some embodiments also include amplifying the target nucleic acid.

Some embodiments include methods of sequencing a target nucleic acid. Some such methods (a) decoding the locations of polynucleotides in an array according to any one of the foregoing methods; (b) hybridizing the target nucleic acid to the capture probes; (c) extending the capture probes hybridized to the target nucleic acid; and (d) detecting the location of the extended capture probes. In some embodiments, (d) detecting the location of the extended capture probes is performed before (a) decoding the locations of polynucleotides in an array. In some embodiments, the capture probes are extended by a ligase. In some embodiments, the capture probes are extended by a polymerase. In some embodiments, the capture probes are extended by the addition of a single nucleotide. Some embodiments also include cleaving the primer binding sites and the barcodes from the capture probes before hybridizing the target nucleic acid to the capture probes. Some embodiments also include cleaving the primer binding sites and the barcodes from the capture probes after hybridizing the target nucleic acid to the capture probes.

Certain Dual Probe Methods

Some embodiments include detecting a target nucleic acid with first and second capture probes. In some embodiments, a target nucleic acid includes a first portion capable of hybridizing to a first capture probe, and a second portion capable of hybridizing to a second capture probe. In some embodiments, a population of beads is obtained in which each bead comprises the first capture probe and the second capture. In some embodiments, one of the two capture probes is attached to the bead via a cleavable linker. In some embodiments, one of the capture probes comprises a detectable label, such as a fluorescent label. In some embodiments, the target nucleic acid hybridizes to the capture probes to generate a double-stranded nucleic acid comprising a single-stranded gap. The gap is filled, and the cleavable linker is cleaved. The extended capture probe is detected. In some embodiments, one of the capture probes comprises a detectable label, such as a fluorescent label. In some embodiments, a detectable label is incorporated into the extended capture probe during the gap-filling.

In some embodiments, the second capture probe is attached to the bead via a cleavable linker, and the second capture probe comprises a detectable label, such as a fluorescent label. Examples of cleavable linkers include linkers that can be cleaved by chemical means, by enzymes such as endonucleases, and by certain frequencies of light. In some embodiments, each bead also includes a first polynucleotide comprising a barcode indicative of the first or second capture probe, and a barcode primer binding site 3' of the barcode. In some embodiments, the first capture probe comprises the first polynucleotide. In some embodiments, the first capture probe is distinct from the first polynucleotide.

In some embodiments, an end of the first capture probe is ligated to an end of the second capture probe. In some embodiments, the first capture probe is ligated to the second capture probe by hybridizing the target nucleic acid to the first and second capture probes of a bead of the population of beads to generate a double-stranded nucleic acid comprising a single-stranded gap between the first and second capture probes, and filing-in the gap between the first and second capture probes. In some embodiments, gap-filling can be performed with a polymerase and/or a ligase. In some embodiments, the cleavable linker is cleaved to generate a bead comprising first capture probe comprising the detectable label. In some embodiments, the population of beads is distributed on a substrate. In some embodiments, the population of beads is distributed on a substrate after the cleavable linker is cleaved. In some embodiments, the population of beads is distributed on a substrate before the cleavable linker is cleaved, or before ligating the first capture probe to the second capture probe. In some embodiments, the location of the bead comprising the first capture probe comprising the detectable label on the substrate is determined.

In some embodiments, decoding the location of the bead comprising the first capture probe comprising the detectable label on the substrate comprises decoding the location of the barcode of the bead comprising the first capture probe comprising the detectable label on the substrate. Some such embodiments can include hybridizing a barcode primer to the barcode primer site, and extending the hybridized barcode primer. In some embodiments, extending the hybridized barcode primer comprises at least one cycle of sequencing by synthesis. In some embodiments, decoding the location of the barcode of the bead comprises sequencing the barcode on the substrate.

In some embodiments, each bead comprises a second polynucleotide comprising an index indicative of the source of the target nucleic acid, and an index primer binding site 3' of the index.

In some embodiments, the population of beads comprises first and second subpopulations of beads, each bead comprising a second polynucleotide comprising an index and an index primer binding site 3' of the index, wherein the indexes of the first subpopulation are different from the indexes of the second subpopulation. In some embodiments, the nucleotide sequences of the indexes of the first subpopulation of beads comprise the same nucleotide sequence, and the nucleotide sequences of the indexes of the second subpopulation of beads comprise the same nucleotide sequence. In some embodiments, the nucleotide sequences of the index primer binding sites comprise the same nucleotide sequence.

In some embodiments, the ligating or cleaving step with the first subpopulation of beads is performed at different locations from the ligating or cleaving step with the second subpopulation of beads. In some embodiments, the different locations comprise different reaction volumes. In some embodiments, the different locations comprise different wells.

Some embodiments also include combining the first and second subpopulations of beads prior to distributing the population of beads on the substrate. In other embodiments, the first subpopulation of beads is distributed on the substrate before the second subpopulation of beads is distributed on the substrate.

In some embodiments, decoding the location of the bead comprising the first capture probe comprising the detectable label on the substrate comprises determining the location of the indexes of the beads comprising a detected capture probe. Some such embodiments include hybridizing a plurality of index primers to the index primer sites, and extending the hybridized index primers. In some embodiments, extending the hybridized index primers comprises at least one cycle of sequencing by synthesis. In some embodiments, decoding the location of the indexes of the beads comprises sequencing the indexes on the substrate.

In some embodiments, the substrate comprises a plurality of discrete sites. In some embodiments, the substrate comprises a plurality of wells. In some embodiments, the substrate comprises a plurality of channels. In some embodiments, a flowcell comprises the substrate. In some embodiments, the distributed population of beads comprise an array.

An embodiment is depicted in FIG. 6B left panel, in which a bead 200 comprises a first capture probe 300 attached to the bead via a cleavable linker 310. A second capture probe 320 is attached to the bead. A target nucleic acid 220 from a certain sample is hybridized to the first and second capture probes, and the first capture probe is extended to fill the gap between the first and second capture probes with nucleotides that include detectable labels 230. After the gap is filled, the target nucleic acid is removed, and the cleavable linker cleaved to generate an extended second capture probe comprising detectable labels attached to the bead. The bead can be distributed on an array on a substrate, and decoded. A polynucleotide comprising an index indicative of the sample attached to the bead, and a polynucleotide comprising a barcode indicative of the first or second capture probes are not shown. Decoding can include determining the location of the detectable label on the array; determining the barcode attached to the bead on the array; and/or determining the index attached to the bead on the array.

Figure 6C:
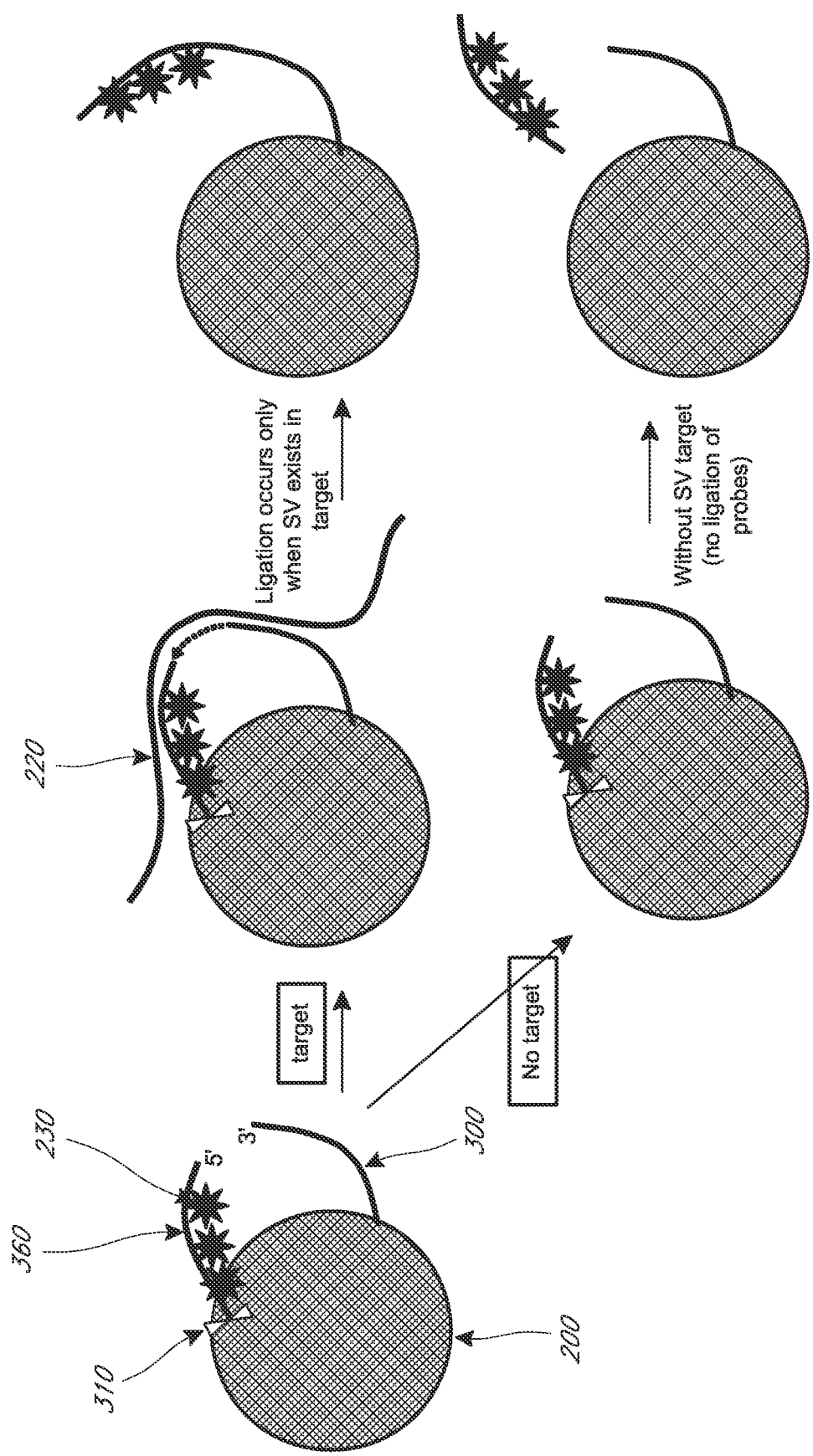
FIG. 6C depicts an example embodiment of a dual probe assay in which a target nucleic acid is hybridized to first and second capture probes on a bead, the first capture probe is ligated to the second capture probe, and a cleavable linker is cleaved to generate a bead comprising an extended first capture probe comprising a detectable label.

An embodiment id depicted in FIG. 6C in which a first capture probe is attached via its 5' end to a bead 200. A second capture probe 360 is attached via its 3' end and a cleavable linker 310 to the bead. The second capture probe includes detectable labels 230. A target nucleic acid 220 is hybridized to the first and second capture probes, the first capture probe is extended and ligated to the second capture probe. In some embodiments, the target nucleic acid can include structural variants (SV). The cleavable linker is cleaved to generate an extended first capture probe comprising detectable label and attached to the bead. The bead can be distributed on an array on a substrate, and decoded. A polynucleotide comprising an index indicative of the sample attached to the bead, and a polynucleotide comprising a barcode indicative of the first or second capture probes are not shown. Decoding can include determining the location of the detectable label on the array; determining the barcode attached to the bead on the array; and/or determining the index attached to the bead on the array. In the absence of a target nucleic acid, the second capture probe and detectable label is cleaved from the bead.

Kits and Systems

Some embodiments include kits and systems for decoding microfeatures, such as polynucleotides on an array. Some such kits and systems can include a substrate, such as chip, or fluidic cell having an array of polynucleotides randomly distributed on a surface of the substrate. The polynucleotides can include a primer binding site 3' of a bar code. In some such embodiments, each polynucleotide can include a capture probe. In more such embodiments, each polynucleotide can be associated with a capture probe through a common element. For example, a polynucleotide and a capture probe can each be bound to the same microfeature, such as a bead.

Some embodiments include a detector adapted to detect signals from reagents hybridized to the polynucleotides in the array; such reagents can include sequencing reagents such as nucleotides comprising detectable labels. Some embodiments include a detector adapted to detect signals that can result from the incorporation of a nucleotide into a polynucleotide, such as pyrophosphate, or changes in hydrogen ions.

Some embodiments include kits or systems comprising at least a first and a second subpopulation of beads. In some embodiments, each bead of a subpopulation can include a first polynucleotide comprising a capture probe, a barcode indicative of the capture probe of the same bead, and a barcode primer binding site 3' of the barcode. In some embodiments each bead of a subpopulation can also include a second polynucleotide comprising an index and an index primer binding site 3' of the index. In some embodiments, the index of a subpopulation of beads can be indicative of that particular subpopulation of beads. In some embodiments, the indexes of the first subpopulation are different from the indexes of the second subpopulation. In some embodiments of the kits and systems provided herein, a first volume comprises the first subpopulation of beads, and a second volume comprises the second subpopulation of beads.

In some embodiments, the capture probes of the first and the second subpopulations of beads each comprise different nucleotide sequences from one another. In some embodiments, the different capture probes of the first and second subpopulations of beads comprise the same nucleotide sequences. In some embodiments, the capture probes comprise a nucleotide sequence capable of hybridizing to a single nucleotide polymorphism (SNP) or complement thereof.

In some embodiments, the barcode primer binding sites comprise the same nucleotide sequence. Some embodiments also include a plurality of barcode primers capable of hybridizing to the barcode primer sites.

In some embodiments, the nucleotide sequences of the indexes of the first subpopulation of beads comprise the same nucleotide sequence, and the nucleotide sequences of the indexes of the second subpopulation of beads comprise the same nucleotide sequence. In some embodiments, the nucleotide sequences of the index primer binding sites comprise the same nucleotide sequence. Some embodiments also include a plurality of index primers capable of hybridizing to the index primer sites.

In some embodiments, the substrate comprises a plurality of discrete sites. In some embodiments, the substrate comprises a plurality of wells. In some embodiments, the substrate comprises a plurality of channels. In some embodiments, a flowcell comprises the substrate. In some embodiments, the substrate is adapted such that a combination of the first and the second subpopulations of beads form an array of beads on a surface of the substrate, and the array is capable of being sequenced in a plurality of sequencing by synthesis cycles.

In some embodiments, the first and second subpopulations of beads each comprises at least 50 capture probes comprising different nucleotide sequences. In some embodiments, the first and second subpopulations of beads each comprises at least 500 capture probes comprising different nucleotide sequences. In some embodiments, the first and second subpopulations of beads each comprises at least 5000 capture probes comprising different nucleotide sequences. In some embodiments, the first and second subpopulations of beads each comprises at least 50000 capture probes comprising different nucleotide sequences.

Some embodiments include at least 10 different subpopulations of beads, each subpopulation comprising an index different from another subpopulation. Some embodiments include at least 100 different subpopulations of beads, each subpopulation comprising an index different from another subpopulation. Some embodiments include at least 1000 different subpopulations of beads, each subpopulation comprising an index different from another subpopulation. Some embodiments include at least 10000 different subpopulations of beads, each subpopulation comprising an index different from another subpopulation.

Some embodiments include a kit comprising: an array of polynucleotides randomly distributed on a surface of a substrate, wherein each polynucleotide comprises a primer binding site 3' of a barcode and is linked to a capture probe, wherein each polynucleotide comprises a different barcode and is linked to a different capture probe. In some embodiments, each polynucleotide is linked to the capture probe via a bead. In some embodiments, each polynucleotide comprises the capture probe In some embodiments, the substrate is planar. In some embodiments, the substrate comprises wells. In some embodiments, the polynucleotides are attached to beads. In some embodiments, the beads are distributed in the wells. In some embodiments, a flow cell comprises the array.

Some embodiments include kits and systems comprising a first and a second subpopulation of beads. In some embodiments, each bead comprises a capture probe which specifically binds to a target ligand. Examples of target ligands include nucleic acids, proteins, or other antigens. Examples of capture probes include nucleic acids, antibodies, and antigen-binding fragments of antibodies. In some embodiments, each bead comprises a first polynucleotide comprising a barcode indicative of the capture probe of the same bead, and a barcode primer binding site 3' of the barcode. In some embodiments, each bead comprises a second polynucleotide comprising an index and an index primer binding site 3' of the index. In some such embodiments, the indexes of the first subpopulation are different from the indexes of the second subpopulation. For example, the indexes of the first subpopulation of beads can be used to distinguish the first subpopulation of beads from the second subpopulation of beads. In some embodiments, the first subpopulation of beads is separate from the second subpopulation of beads. For example, a first volume comprises the first subpopulation of beads and a second volume comprises the second subpopulation of beads.

In some embodiments, the capture probe comprises a nucleic acid, and the target ligand comprises a target nucleic acid. In some such embodiments, the first polynucleotide comprises the capture probe. In some embodiments, the capture probes comprise a nucleotide sequence capable of hybridizing to a single nucleotide polymorphism (SNP) or complement thereof.

In some embodiments, the capture probe comprises an antibody or antigen binding fragment of an antibody.

In some embodiments, the capture probes of the first and the second subpopulations of beads each specifically bind to different target ligands from one another. For example, the capture probes of the first subpopulation of beads each specifically bind to different target ligands from one another; and the capture probes of the second subpopulation of beads each specifically bind to different target ligands from one another. In some embodiments, the different capture probes of the first and second subpopulations of beads specifically bind to the same target ligands. For example, the set of different capture probes of the first subpopulation of beads specifically bind to the same target ligands as the set of different capture probes of the first subpopulation of beads.

In some embodiments, the barcode primer binding sites comprise the same nucleotide sequence. Some embodiments also include a plurality of barcode primers capable of hybridizing to the barcode primer sites.

In some embodiments, the nucleotide sequences of the indexes of the first subpopulation of beads comprise the same nucleotide sequence, and/or the nucleotide sequences of the indexes of the second subpopulation of beads comprise the same nucleotide sequence. In some embodiments, the nucleotide sequences of the index primer binding sites comprise the same nucleotide sequence. Some embodiments also include a plurality of index primers capable of hybridizing to the index primer sites.

In some embodiments, the substrate comprises a plurality of discrete sites. In some embodiments, the substrate comprises a plurality of wells. In some embodiments, the substrate comprises a plurality of channels. In some embodiments, a flowcell comprises the substrate. In some embodiments, the substrate is adapted such that a combination of the first and the second subpopulations of beads form an array of beads on a surface of the substrate, and the array is capable of being sequenced in a plurality of sequencing by synthesis cycles.

In some embodiments, the first and second subpopulations of beads each comprises at least 50, 100, 500, 1000, or 5000 capture probes different from one another, or any number of capture probes between any two of the foregoing numbers. Some embodiments also include at least 5, 10, 20, 50, 100, 200, 500, 1000 different subpopulations of beads, each subpopulation comprising an index different from another subpopulation, or any number of different subpopulations of beads between any two of the foregoing numbers.

Some embodiments include a kit comprising a first and a second subpopulation of beads, wherein each bead comprises: a capture probe which specifically binds to a target ligand, a first polynucleotide comprising a barcode indicative of the capture probe, and a barcode primer binding site 3' of the barcode, and a second polynucleotide comprising an index and an index primer binding site 3' of the index, wherein the indexes of the first subpopulation are different from the indexes of the second subpopulation, wherein a first volume comprises the first subpopulation of beads, and a second volume comprises the second subpopulation of beads. In some embodiments, the capture probe comprises a nucleic acid, and the target ligand comprises a target nucleic acid. In some embodiments, the first polynucleotide comprises the capture probe. In some embodiments, the capture probes of the first and the second subpopulations of beads each comprise different nucleotide sequences from one another. In some embodiments, the different capture probes of the first and second subpopulations of beads comprise the same nucleotide sequences. In some embodiments, the capture probe comprises an antibody or antigen binding fragment thereof. In some embodiments, the capture probes of the first and the second subpopulations of beads each specifically bind to different target ligands from one another. In some embodiments, the different capture probes of the first and second subpopulations of beads specifically bind to the same target ligands. In some embodiments, the barcode primer binding sites comprise the same nucleotide sequence. Some embodiments also include a plurality of barcode primers capable of hybridizing to the barcode primer sites. In some embodiments, the nucleotide sequences of the indexes of the first subpopulation of beads comprise the same nucleotide sequence, and the nucleotide sequences of the indexes of the second subpopulation of beads comprise the same nucleotide sequence. In some embodiments, the nucleotide sequences of the index primer binding sites comprise the same nucleotide sequence. Some embodiments also include a plurality of index primers capable of hybridizing to the index primer sites. In some embodiments, a flowcell comprises the substrate. In some embodiments, the substrate is adapted such that a combination of the first and the second subpopulations of beads form an array of beads on a surface of the substrate, and the array is capable of being sequenced in a plurality of sequencing by synthesis cycles. In some embodiments, the first and second subpopulations of beads each comprises at least 50 capture probes different from one another. In some embodiments, the first and second subpopulations of beads each comprises at least 500 capture probes different from one another. Some embodiments also include at least 10 different subpopulations of beads, each subpopulation comprising an index different from another subpopulation.

EXAMPLES

Example 1

Decoding an Array by Sequencing

A plurality of polynucleotides are synthesized, each polynucleotide comprises 5' to 3': a spacer, a unique barcode, a primer binding site, and a unique capture probe. The sequences of the barcode and capture probe are known; the sequence of the primer binding site is the same for each polynucleotide. Each polynucleotide is attached to a bead. The beads are randomly distributed into the wells of a chip. The bead array is decoded by hybridizing a primer to the primer binding site, extending the primer, and detecting the sequence of the barcode. The location of the barcode identifies the location of the associated capture probe.

Example 2

Decoding Barcodes on an Array by Sequencing

A nucleic acid library prepared from human genomic DNA was prepared. A subpopulation of beads was prepared. A first and second polynucleotide was attached to each bead. The first polynucleotide included a capture probe, a barcode primer binding site, and a barcode indicative of the capture probe. The second polynucleotide included an index and an index primer binding site.

Figure 7A:
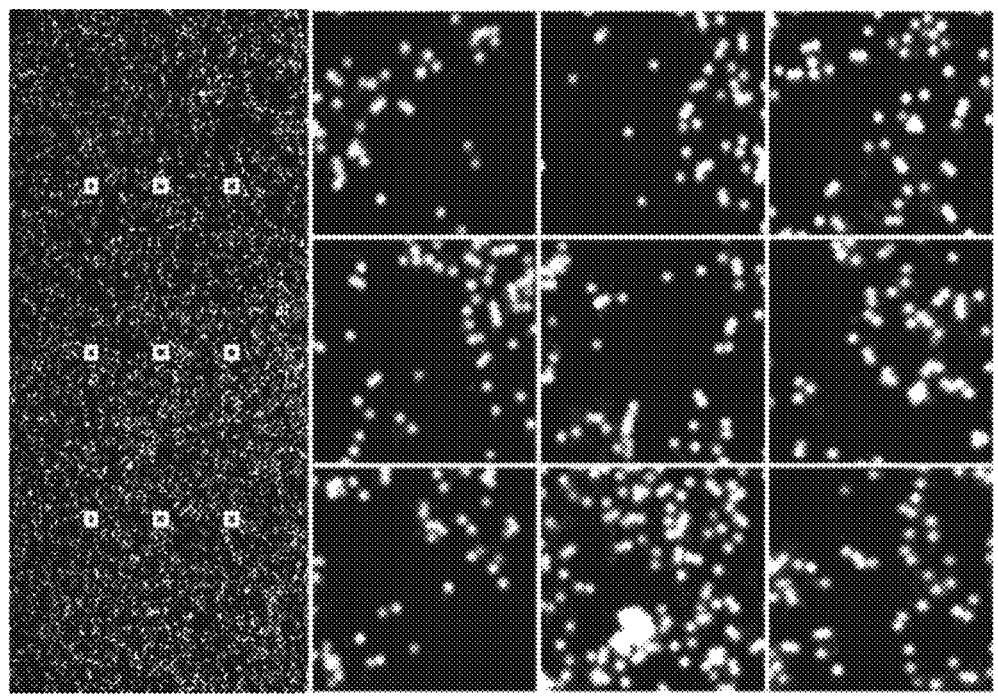
FIG. 7A is a photograph of a bead pool immobilized on a flow cell.
Figure 7B:
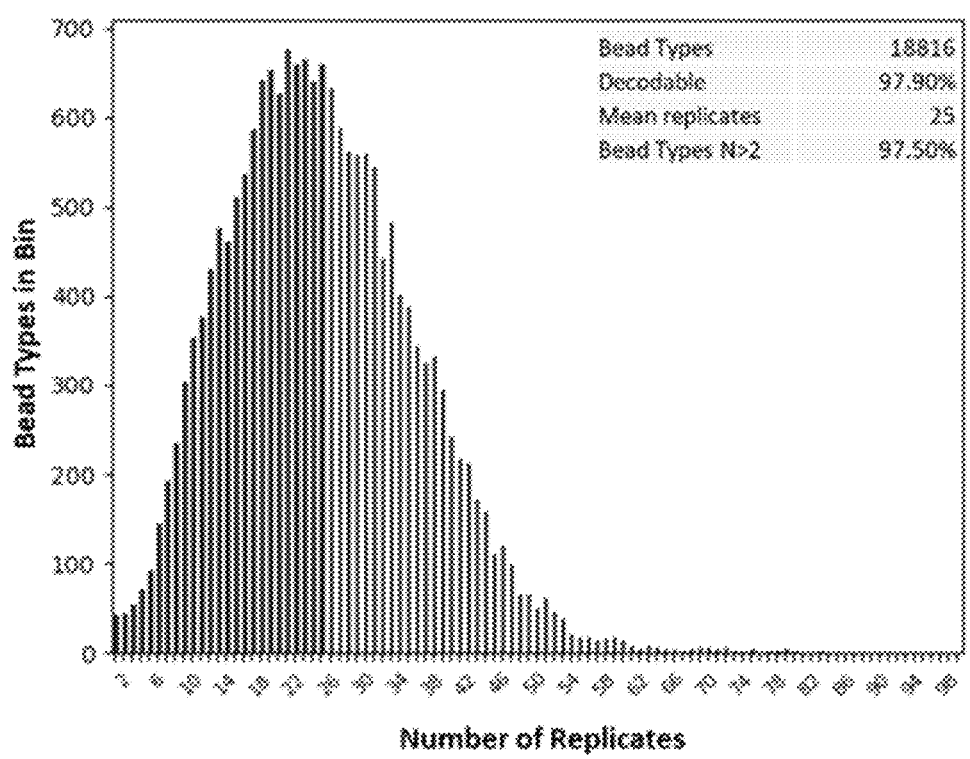
FIG. 7B is a bar graph of the number of replicates for certain bead types in certain bins.

A bead pool containing 18816 different code/probe types was loaded onto a HiSeq flow cell (FIG. 7A). After immobilization, 20 nucleotide long codes were sequenced using SBS chemistry and the identity of each bead was determined by aligning code sequences to a list of bead types. FIG. 7B is a histogram of the number of replicates for certain bead types in certain bins, and showed that 97.5% of the expected content is identified using a sequencing based decode process and that the vast majority of bead types are present at a level sufficient for genotyping studies.

Example 3

Genotyping Performance on HiSeq using FFN Detection

Figure 7C:
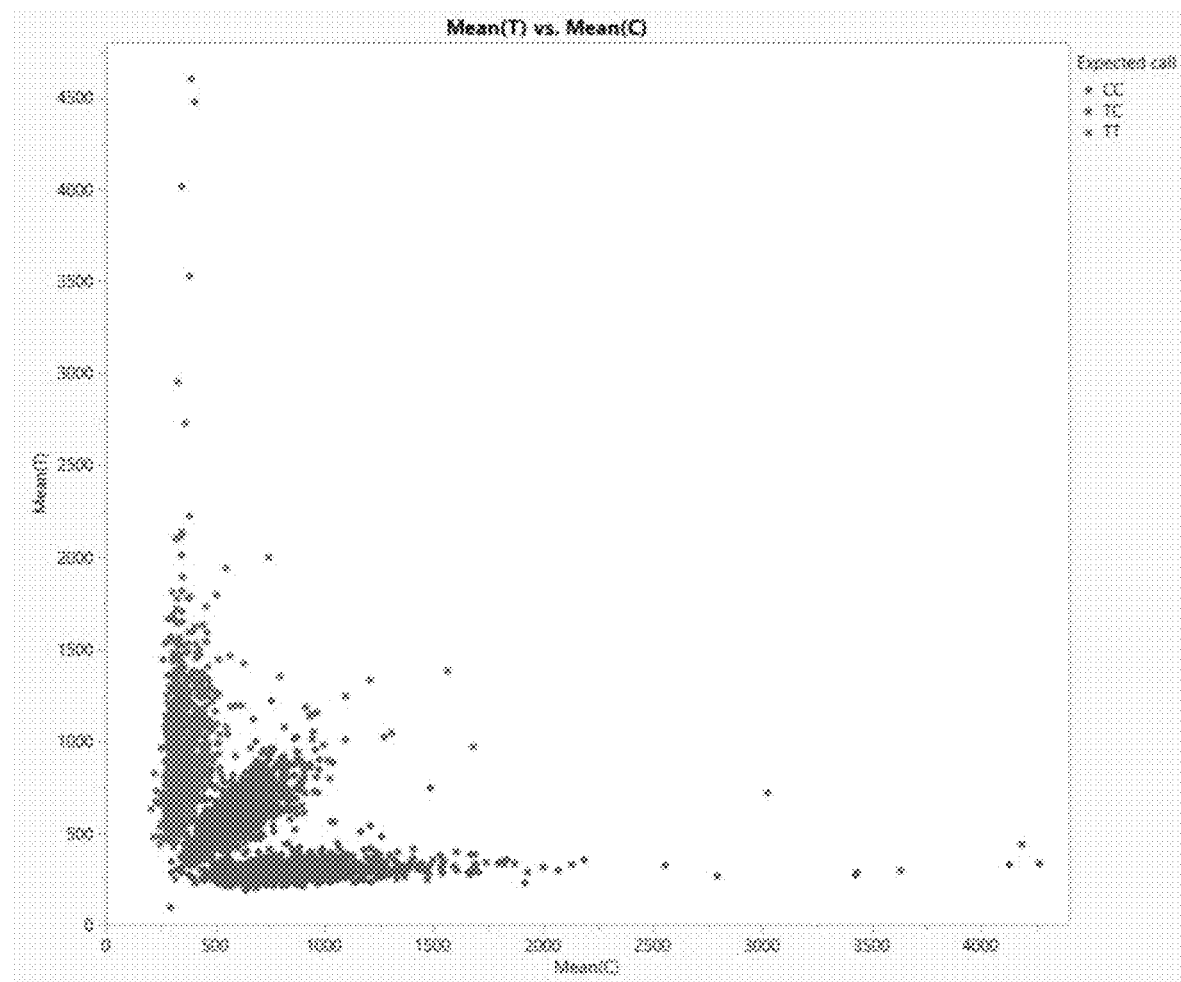
FIG. 7C is a graph of mean C intensity vs mean T intensity. The mean C intensity is the intensity of the fluorescence coming from labeled cytosine in a pair of nucleotides and the mean T intensity is the intensity of the fluorescence from labeled thymidine in a pair of nucleotides.

To demonstrate genotyping performance on HiSeq using FFN detection, oligonucleotide target DNA was hybridized to a suspension of beads with conjugated to probe oligos. Beads were loaded onto a HiSeq flow cell. Probes bound to target DNA were extended by a single base using fluorescent nucleotides. The bead loaded flow cell was imaged to obtain genotyping bead intensities. Fluorescent nucleotides were cleaved and beads were decoded using SBS chemistry. Decode and genotyping reads were aligned to measure assay performance. Individual points were colored according to the expected genotype. FIG. 7C is a graph of C intensity vs T intensity, where each point is the average of all replicates for a given bead type and are colored according to expected genotype and showed that a single base probe extension with fluorescent nucleotides enables accurate genotyping.

Example 4

Multiplexing 12 Samples with a 10,368-Plex Bead Pool

Figure 8:
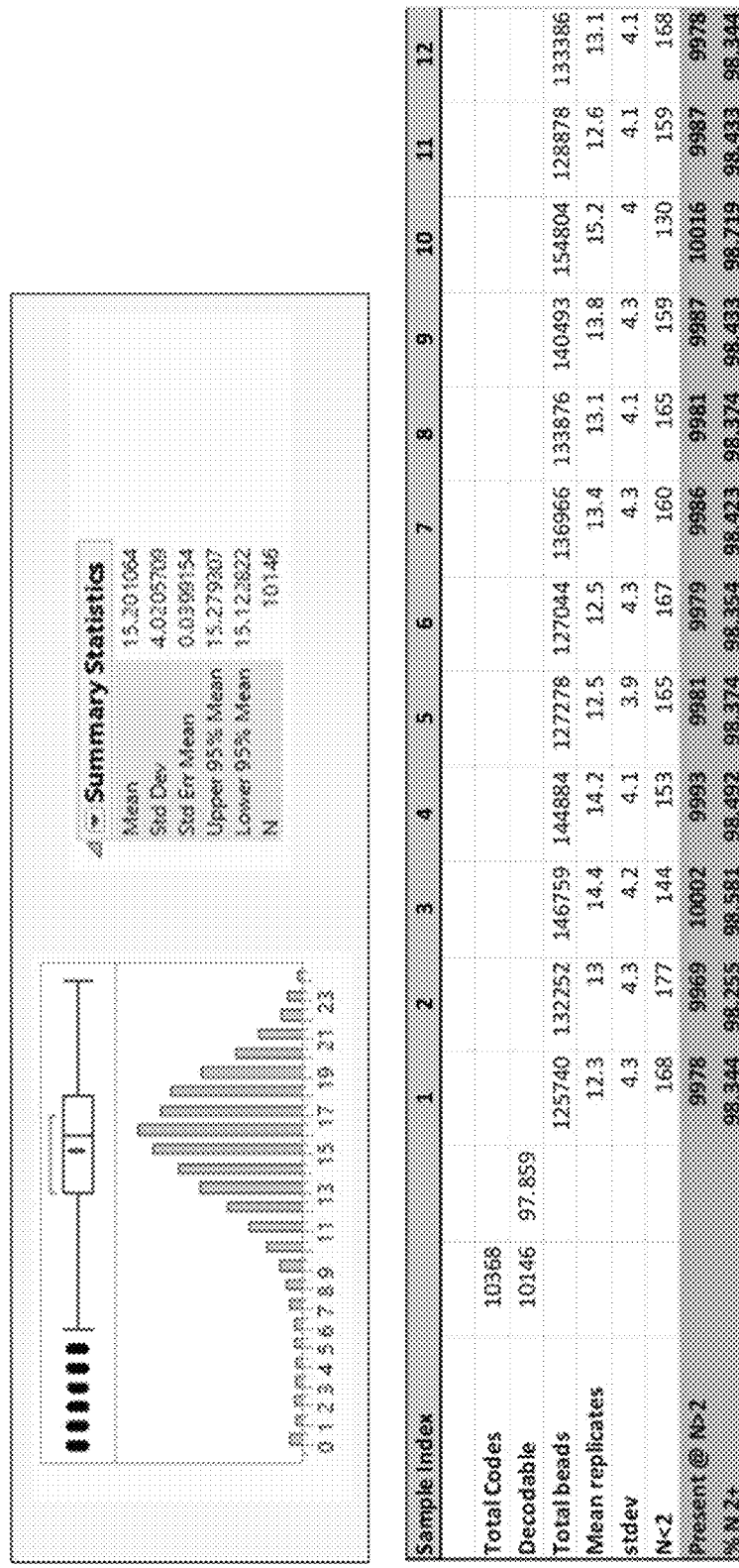
FIG. 8 is a histogram of the number of certain bead types in certain bins for a representative sample.

This example demonstrates demultiplex multiple samples on a single flow cell, and in particular, the ability to multiplex 12 samples with a 10,368-plex bead pool. A single bead pool was separately hybridized to 12 different index sequences. After hybridization, samples were pooled and loaded on a HiSeq flow cell. Two separate reads were then performed, one to identify the sample based on the hybridized index and a separate read to identify the bead type based on the decode read. FIG. 8 is a histogram of the number of certain bead types in certain binds for a representative sample, and showed that the majority of bead types are present at a level sufficient for genotyping experiments for a given sample. The table in FIG. 7 is a summary of the consistency of demultiplexing and decoding beads across 12 indexed samples pooled and loaded simultaneously demonstrating that sample representation is uniform and that the majority of probes are present across all samples The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:
1. A method for identifying target ligands in an array comprising:
   (a) obtaining a first and a second subpopulation of beads, wherein each bead comprises:
      (i) a capture probe capable of specifically binding to a target ligand,
      (ii) a first polynucleotide comprising a barcode, wherein the barcode is indicative of the capture probe, and

(iii) a second polynucleotide comprising an index, wherein each index of the first subpopulation of beads is different from each index of the second subpopulation of beads;
(b) specifically binding first target ligands to the capture probes of the first subpopulation of beads in a first reaction volume, and specifically binding second target ligands to the capture probes of the second subpopulation of beads in a second reaction volume; and
(c) distributing the first and the second subpopulations of beads comprising the specifically bound first and second target ligands on a surface of a substrate, thereby obtaining an array of beads;
(d) detecting in the array the specifically bound first and second target ligands of the first and the second subpopulations of beads;
(e) sequencing the barcodes in the array of beads;
(f) sequencing the indexes in the array of beads; and
(g) decoding the locations of beads in the array of beads comprising a detected target ligand in the array, thereby identifying target ligands in the array of beads.

2. The method of claim 1, wherein step (b) further comprises combining the first and the second subpopulations of beads comprising the specifically bound first and second target ligands, prior to step (c).

3. The method of claim 1, wherein the capture probe comprises a nucleic acid.

4. The method of claim 1, wherein the capture probe comprises an antibody or antigen binding fragment thereof.

5. A method for identifying target ligands in an array comprising:
(a) obtaining a substrate having an array of beads distributed on a surface of the substrate, wherein the array of beads comprises a first and a second subpopulation of beads, comprising:
(i) obtaining the first and the second subpopulation of beads, wherein each bead comprises:
a capture probe capable of specifically binding to a target ligand,
a first polynucleotide comprising a barcode, and a primer binding site 3' of the barcode, wherein the barcode is indicative of the capture probe, and
a second polynucleotide comprising an index and an index primer binding site 3' of the index, wherein each index of the first subpopulation of beads is different from each index of the second subpopulation of beads;
(ii) specifically binding first target ligands to the capture probes of the first subpopulation of beads in a first reaction volume, and specifically binding second target ligands to the capture probes of the second subpopulation of beads in a second reaction volume; and
(iii) distributing the first and the second subpopulations of beads comprising the specifically bound first and second target ligands on the substrate, thereby obtaining the substrate having an array of beads;
(b) detecting in the array the specifically bound first and second target ligands of the first and the second subpopulations of beads;
(c) sequencing the barcodes of the first and the second subpopulations of beads by hybridizing a plurality of primers to the barcode primer binding sites of the first and the second subpopulations of beads;
and extending the hybridized primers, thereby determining the location of the capture probes of the first and the second subpopulations of beads in the array;
(d) sequencing the indexes of the first and the second subpopulations of beads, thereby determining the locations of the first and the second subpopulations of beads in the array; and
(e) decoding the locations of beads of the array of beads comprising a detected target ligand in the array, thereby identifying target ligands of the first target ligands or of the second target ligands in the array.

6. The method of claim 5, wherein the first and second target ligands each comprise a nucleic acid, and wherein step (a) further comprises:
(iv) extending the capture probes specifically bound to the first and second target ligands.

7. The method of claim 6, wherein step (iv) comprises contacting the capture probes of the first and the second subpopulations of beads with a polymerase.

8. The method of claim 6, wherein step (iv) is performed prior to step (iii).

9. The method of claim 6, wherein step (iv) comprises performing at least one cycle of sequencing by synthesis.

10. The method of claim 5, wherein the first polynucleotide comprises the capture probe.

11. The method of claim 10, wherein the capture probes of the first subpopulation of beads comprise different nucleotide sequences from the capture probes of the second subpopulation of beads.

12. The method of claim 10, wherein the capture probes of the first subpopulation of beads comprise the same nucleotide sequences as the capture probes of the second subpopulation of beads.

13. The method of claim 5, wherein the first subpopulation of beads comprising the specifically bound first target ligands is distributed on the substrate before the second subpopulation of beads comprising the specifically bound second target ligands is distributed on the substrate.

14. The method of claim 5, wherein the first and second target ligands are obtained from different subjects.

15. The method of claim 5, further comprising at least 10 different subpopulations of beads, each subpopulation comprising an index different from another subpopulation.

16. The method of claim 5, wherein step (ii) further comprises combining the first and the second subpopulations of beads comprising the specifically bound first and second target ligands.

17. The method of claim 5, wherein the capture probe comprises a nucleic acid.

18. The method of claim 5, wherein the capture probe comprises an antibody or antigen binding fragment thereof.

19. The method of claim 18, wherein step (b) comprises contacting the first and second target ligands specifically bound to the capture probes of the first and the second subpopulations of beads with a secondary antibody or antigen-binding fragment thereof, wherein the secondary antibody or antigen-binding fragment thereof comprises a detectable label.

20. The method of claim 5, wherein a flowcell comprises the substrate.

* * * * *

UNITED STATES PATENT AND TRADEMARK OFFICE
CERTIFICATE OF CORRECTION

PATENT NO. : 11,667,957 B2
APPLICATION NO. : 16/661885
DATED : June 6, 2023
INVENTOR(S) : Darren Segale et al.

It is certified that error appears in the above-identified patent and that said Letters Patent is hereby corrected as shown below:

In the Specification

In Column 10, Line 15, delete "Hoogstein" and insert --Hoogsteen--.

In Column 12, Line 32, delete "in in" and insert --in--.

In Column 30, Line 32, delete "samples" and insert --samples.--.

In the Claims

In Column 32, Claim 5, Line 2, delete "beads;" and insert --beads--.

Signed and Sealed this
Twenty-second Day of August, 2023

Katherine Kelly Vidal
*Director of the United States Patent and Trademark Office*